(12) United States Patent
Park et al.

(10) Patent No.: US 8,658,672 B2
(45) Date of Patent: Feb. 25, 2014

(54) HIF-1α ACTIVATING AGENT

(75) Inventors: Hyunsung Park, Sungnam-si (KR); Su Mi Choi, Seoul (KR)

(73) Assignee: University of Seoul Foundation of Industrial and Academic Cooperation, Seoul (KR)

( * ) Notice: Subject to any disclaimer, the term of this patent is extended or adjusted under 35 U.S.C. 154(b) by 1647 days.

(21) Appl. No.: 12/094,748

(22) PCT Filed: Jan. 15, 2007

(86) PCT No.: PCT/KR2007/000242
§ 371 (c)(1),
(2), (4) Date: May 22, 2008

(87) PCT Pub. No.: WO2007/086663
PCT Pub. Date: Aug. 2, 2007

(65) Prior Publication Data
US 2009/0048294 A1 Feb. 19, 2009

(30) Foreign Application Priority Data
Jan. 24, 2006 (KR) .................. 10-2006-0007303

(51) Int. Cl.
*A61K 31/47* (2006.01)

(52) U.S. Cl.
USPC ....................................... 514/311

(58) Field of Classification Search
USPC ........................................ 514/311
See application file for complete search history.

(56) References Cited

U.S. PATENT DOCUMENTS

2007/0092500 A1* 4/2007 Frey et al. .................. 424/93.21

FOREIGN PATENT DOCUMENTS

| WO | WO97/44036 | 11/1997 |
| WO | WO01/82911 | 11/2001 |
| WO | WO03/077901 | 9/2003 |
| WO | WO2004/007461 A1 * | 1/2004 |

OTHER PUBLICATIONS

Lando et al. (Genes & Development, vol. 16, pp. 1466-1471; 2002).*
Li et al. (Advances in Skin & Wound Care, vol. 18, No. 9, abstract; Nov./Dec. 2005).*

* cited by examiner

*Primary Examiner* — Kevin E Weddington
(74) *Attorney, Agent, or Firm* — Klarquist Sparkman, LLP

(57) ABSTRACT

The present invention relates to a HIF-1α activator containing clioquinol and its derivatives as an active ingredient. Clioquinol and its derivatives of the invention inhibit HIF-1α (hypoxia-inducible factor-1α) ubiquitination in normoxic cells and thus accumulate HIF-1α. In the meantime, CQ inhibits FIH-I activity and thereby induces transcription activity of the accumulated HIF-1α, resulting in the induction of expressions of HIF-1α target genes VEGF (vascular endothelial growth factor) and EPO (erythropoietin). Therefore, clioquinol and its derivatives can be effectively used as a therapeutic agent for ischemic disease.

8 Claims, 18 Drawing Sheets

| | Chemical name | Molecular Weight |
|---|---|---|
| CQ | 5-chloro-7-iodo-8-quinol (Clioquinol) | 305.50 |
| A | 5-chloroquinolin-8-yl acetate (Chloroacetoxy quinoline) | 221.64 |
| B | 5,7-diiodo-8-hydroxyquinoline (Iodoquinol) | 396.95 |
| C | 5,7-Dibromo-8-hydroxyquinoline (Broxyquinoline) | 302.95 |
| D | 8-hydroxyquinoline (Hydroxyquinol) | 145.16 |

A

B

A

B

A

B

| | Chemical name | Molecular Weight |
|---|---|---|
| CQ | 5-chloro-7-iodo-8-quinolinol, (Clioquinol) | 305.50 |
| B | 5,7-diiodo-8-hydroxyquinoline, (Iodoquinol) | 396.95 |

HIF-1α ACTIVATING AGENT

CROSS REFERENCE TO RELATED APPLICATIONS

This is the U.S. National Stage of International Application No. PCT/KR2007/000242, filed Jan. 15, 2007, which was published in English under PCT Article 21(2), which in turn claims the benefit of Korean Application No. 10-2006-0007303, filed Jan. 24, 2006. Both applications are incorporated herein in their entirety.

TECHNICAL FIELD

The present invention relates to a HIF-1α activating agent containing clioquinol and its derivatives as an active ingredient. The clioquinol and its derivatives of the present invention can be effectively used for the treatment of ischemic diseases since clioquinol and its derivatives are able to inhibit HIF-1α ubiquitation under normoxic condition to accumulate HIF-1α and inhibit FIH-1 activity to lead the transcriptional activity of the accumulated HIF-1α and thereby induce the expressions of VEGF and EPO, target genes of HIF-1α.

BACKGROUND ART

Ischemia indicates a local anemia which is caused by clogging or narrowing of blood vessels. Every part of human body needs to be supplied enough oxygen and nutrition through blood vessels to be functioning normally. The heart also needs to be provided with oxygen and nutrition through the blood vessel called the coronary artery. With insufficient blood flow, metabolites are accumulated in the myocardium, leading to hypoxia with causing functional disorder. This case is called myocardial ischemia and the heart failure resulted from the myocardial ischemia is called ischemic heart disease, which is largely represented by angina pectoris and myocardial infraction. In general, the incidence of such heart disease is higher in male than in female, as being older and in those having risk factors. Once ischemia is developed, blood vessels are apt to be blocked, resulting in the said diseases, for example the interruption of brain vessels results in ischemic heart disease. Once the blood circulation is interrupted by ischemia, terminal regions are going to be in trouble too, that is terminal tissues are necrotized to cause ischemic limb injury. As explained above, ischemia is a trigger for various diseases, so it is an urgent request to develop a therapeutic agent targeting ischemia.

HIF-1 (hypoxia-inducible factor-1) is a key regulator of hypoxic adaptation that functions by activating the transcription of several genes involved in angiogenesis, erythropoiesis, and glycolysis (Masson and Ratcliffe, *J Cell Sci* 116: 3041-3049, 2003; Seagroves et al, *Mol Cell Biol* 21:3436-3444, 2001). It consists of two subunits; HIF-1α is rapidly degraded under normoxic condition by the ubiquitin-proteasome system, whereas HIF-1β is stable (Huang et al., *Proc Natl Acad Sci USA* 95:7978-7992, 1998; Kallio et al, *J Biol Chem* 274:6519-6525, 1999). Under normoxic conditions the proline-564 and/or 402 residues of HIF-1α are hydroxylated by PHDs (HIF-1α-specific prolyl-4-hydroxylases) and thus inhibited, which needs $O_2$, 2-oxoglutarate, vitamin C and $Fe^{2+}$ (Bruikc and McKnight, *Science* 294:1337-1340, 2001; Epstein et al., *Cell* 107:43-54, 2001; Ivan et al., *Science* 292:464-468, 2001; Jaakkola et al., *Science* 292:468-472, 2001; Masson et al., *EMBO J* 20:5197-5206, 2001). PHD1 (HPH3, EGLN2), PHD2 (HPH2, EGLN1) and PHD3 (HPH1, EGLN3) are the PHD family found in mammalian cells (Huang et al., *J Biol Chem* 277:39792-39800, 2002; Talyer, *Gene* 275:125-132, 2001). The hydroxylated prolines interact with VHL (von Hippel-Lindau) protein, a component of E3 ubiquitin ligase, and the HIF-1α is ubiquitinated by the VCB E3 ubiquitin-ligase complex (VHL protein, Elongin B, Elongin C, Cul2 and Rbx1) (Iwai et al., *Proc Natl Acad Sci USA* 96:12436-12441, 1999; Kamura et al, *Science* 284:657-661, 1999). In hypoxic conditions, proline hydroxylation decreases and HIF-1α accumulates. The accumulated HIF-1α migrates to the nucleus to interact with HIF-1β in order to be activated as a transcription factor. HIF-1α/β hetero-complex binds to HRE (hypoxia-responsive elements) located in the promoter region of a target gene and to transcription co-factors such as p300/CBP and thus increases the expressions of target genes necessary for angiogenesis and intracellular oxygen supply (Nathali et al., *Biochem Pharmacol.* 68:971-980, 2004).

Oxygen molecules inhibit not only the stabilization of HIF-1α but also its transcription activity, since FIH-1 (factor inhibiting HIF-1α) catalyzes hydroxylation of the asparagine-803 residue of HIF-1α. Hydroxylation of the asparagine residue in the transactivation domain of HIF-1α prevents it from recruiting its coactivator CBP and thus induces the accumulation of non-functional HIF-1α. FIH-1 has been recently identified and followingly its activity and tertiary structure have also been identified (Lee et al., *J. Biol. Chem.* 278:7558-7563, 2003; Elkins et al., *J. Biol. Chem.* 278:1802-1806, 2003). Like PHD, FIH-1 also recruits $Fe^{2+}$ as a cofactor and catalyzes hydroxylation of the asparagine-803 residue of HIF-1α using $O_2$ and 2-oxoglutarate (Lando et al., *Science* 295:858-865, 2002). FIH-1 has at least 2-fold lower Km for 2-oxoglutarate and oxygen than PHD indicating that it is functioning even under inoperable oxygen pressure (Koivunen et al., *J. Biol. Chem.* 279:9899-9904, 2004).

Target genes of HIF-1α, EPO (erythropoietin) and VEGF (vascular endothelial growth factor) act as an important mediator of protective mechanism under hypoxic condition (Grimm et al., *Nat Med* 8:178-724, 2002: Calvillo et al., *Proc Natl Acad Sci USA* 100:4802-4806, 2003: Ferriero D. M., *Epilepsia.* 46:45-51, 2005; Simons, A., Ware, J. A., *Nat Rev Drug Discov.* 2:863-871, 2003). EPO and its receptor are expressed in the brain and thus involved in neuroprotection in relation to cerebral infarction associated brain damage (Digicayolioglu, M. et al., *Proc Natl Acad Sci USA* 92:3717-3720, 1995; Ehrenreich, H. et al., *Metab Brain Dis.* 19:195-206, 2004), that is they presumably protect neurons when cerebral infarction is developed in vivo (Sasaki et al., *Proc Natl Acad Sci USA* 95:4635-4640, 1998). VEGF has also been evaluated as a stable therapeutic agent for myocardial infarction (Yoon, Y. S. et al., *Mol Cell Biochem.* 264:1494-1504, 2004; Shah, P. B. and Losordo, D. W., *Adv Genet.* 54:339-361, 2005; Simons, M. and Ware J. A., *Nat Rev Drug Discov.* 2:863-871, 2003; Henry, T. D. et al., *Circulation* 107:1359-1365, 2003). VEGF has a protective activity to neuron and neuroglia damaged by angiogenesis (Rosenstein, J. M. and Krum, K, *Exp Neurol* 187:246-253, 2004). When VEGF level is decreased, amyotrophic lateral sclerosis is developed and perfusion and neuroprotection functions are reduced (Storkebaum, E., Lambrechts, D., Carmeliet, P., *Bioessays* 26:943-954, 2004).

Clioquinol (referred as "CQ" hereinafter) is involved in selective chelation of heavy metal ions such as $Zn^{2+}$, $Cu^{2+}$ and $Ca^{2+}$ and regulates the effects of such metal ions on enzyme activity and protein formation. pKa values of CQ are as follows: $Cu^{2+}$, 15.8; $Zn^{2+}$, 12.5; $Ca^{2+}$, 8.1; $Mg^{2+}$, 8.6 (Agrawal, Y. K. et al., *J Pharm Sci.* 75:190-192, 1986). CQ is hydrophobic and able to cross the blood-brain barrier. CQ has been re-evaluated as the prototype metal-protein attenuating compound that reduces metalloprotein precipitation in Alzheimer's disease, Parkinson's disease and Huntington's diseases and oxidative stress thereby. CQ was extensively used as an antibiotic in the mid-1900s, but then withdrawn because it caused subacute myelo-optic neuropathy in Japan (Chery, R. A., *Neuron* 30:665-676, 2001; Kaur, D. et al., *Neuron* 37:899-909, 2003; Nguyen T. et al., *Proc Natl Acad Sci USA* 102:11840-11845, 2005). In a study of APP2576 transgenic mice which have an Alzheimer's disease-type neuropathy, CQ reduced both amyloid beta plaques and serum levels of amyloid beta, without systemic adverse effects (Doraiswamy, P. M. et al., *Lancet Neorul* 3:431-434, 2004). A recent phase II clinical trial in 36 patients with Alzheimer's disease showed that CQ slowed cognitive decline and decreased plasma amyloid beta concentrations (Ritchie C. W. et al., *Arch Neurol* 60:1685-1691, 2003).

CQ also causes apoptotic cell death in several human cancer cell lines. The addition of copper or zinc to the CQ treated cancer cell lines did not prevent cell death and rather increased the apoptotic cell death. CQ treated cells were fluorescence-labeled to detect the level of zinc. And from the result was confirmed that CQ induced cell death by activating zinc ionophore (Ding, W. O., et al., *Cancer Res.* 65:3389-3395, 2005).

TPEN (tetrakis-(2-pyridylmethyl)ethanediamine: C26H28N6) is also a metal chelator like CQ, which is involved in the selective chelation of heavy metal ions such as $Zn^{2+}$, $Cu^{2+}$ and $Fe^{2+}$ and regulates the effects of such ions on enzyme activity and protein formation. pKa values of TPEN are as follows: $Cu^{2+}$, 20.2; $Zn^{2+}$, 15.4; $Fe^{3+}$, 14.4; $Ca^{2+}$, 3 (Chemy R. A. et al., *J Biol Chem.*, 274:23223-23228, 1999).

DISCLOSURE

Technical Problem

It is an object of the present invention to provide a novel use of clioquinol or its derivatives as a therapeutic agent for ischemic disease.

Technical Solution

To achieve the above object, the present invention provides a HIF (Hypoxia inducible factor)-1α activating agent containing clioquinol or its derivatives as an active ingredient.

The present invention also provides a FIH-1 (factor inhibiting HIF-1α) inhibitor containing clioquinol or its derivatives as an active ingredient.

The present invention further provides a VEGF (vascular endothelial growth factor) expression inducer containing clioquinol or its derivatives as an active ingredient.

The present invention also provides an EPO (erythropoietin) expression inducer containing clioquinol or its derivatives as an active ingredient.

The present invention also provides a therapeutic agent for ischemic disease containing clioquinol or its derivatives as an active ingredient.

The present invention also provides an angiogenesis inducer containing clioquinol or its derivatives as an active ingredient.

The present invention provides a treatment method for ischemic disease containing the step of administering the effective dose of clioquinol or its derivatives to an ischemia patient.

The present invention also provides a novel use of clioquinol or its derivatives for the production of a therapeutic agent for ischemic disease.

Hereinafter, the present invention is described in detail.

The present invention provides a HIF (Hypoxia inducible factor)-1α activating agent containing clioquinol or its derivatives as an active ingredient.

The present invention also provides a FIH-1 (factor inhibiting HIF-1α) inhibitor containing clioquinol or its derivatives as an active ingredient.

The present invention further provides a VEGF (vascular endothelial growth factor) expression inducer containing clioquinol or its derivatives as an active ingredient.

The present invention also provides an EPO (erythropoietin) expression inducer containing clioquinol or its derivatives as an active ingredient.

Clioquinol (referred as "CQ" hereinafter: Formula 2) is a heavy metal chelator, which selectively chelates such heavy metal ions as $Zn^{2+}$, $Cu^{2+}$ and $Ca^{2+}$ and is also involved in the regulation of the effects of such metal ions on enzyme activity and protein formation. pKa values of CQ are as follows: $Cu^{2+}$, 15.8; $Zn^{2+}$, 12.5; $Ca^{2+}$, 8.1; $Mg^{2+}$, 8.6.

CQ or its derivatives have the structure of the following Formula 1.

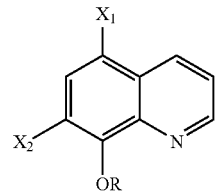

<Formula 1>

R is H or acetyl, $X_1$ and $X_2$ are independently H or halogen.

The halogen is preferably F, Br, Cl or I.

CQ (Formula 2) derivatives are exemplified by 5-chloroquinolin-8-yl acetate (Formula 3), 5,7-diiodo-8-hydroxyquinoline (Formula 4), 5,7-dibromo-8-hydroxyquinoline (Formula 5), and 8-hydroxyquinoline (Formula 6), and the formulas are as follows.

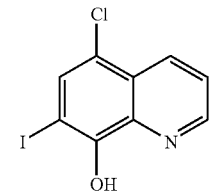

<Formula 2>

5-chloro-7-iodo-8-quinolinol
(clioquinol) mw 305.50

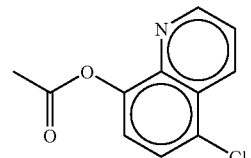

<Formula 3>

5-chloroquinolin-8-yl acetate
(chloroacetoxy quinoline) mw 221.64

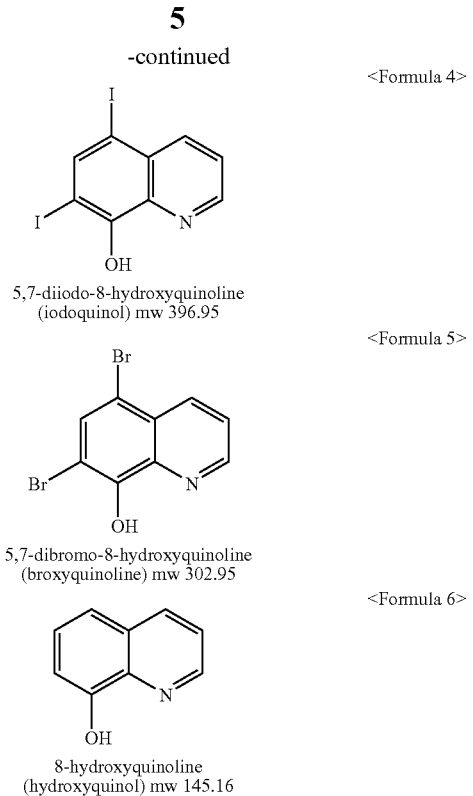

5,7-diiodo-8-hydroxyquinoline
(iodoquinol) mw 396.95

5,7-dibromo-8-hydroxyquinoline
(broxyquinoline) mw 302.95

8-hydroxyquinoline
(hydroxyquinol) mw 145.16

TPEN (tetrakis-(2-pyridylmethyl)ethanediamine: C26H28N6) also selectively chelates such heavy metal ions as $Zn^{2+}$, $Cu^{2+}$ and $Fe^{2+}$ and is involved in the regulation of the effects of the metal ions on enzyme activity and protein formation. pKa values of TPEN are as follows: $Cu^{2+}$, 20.2; $Zn^{2+}$, 15.4; $Fe^{3+}$, 14.4; $Ca^{2+}$, 3 (Chemy R. A. et al., *J Biol Chem.* 274:23223-23228, 1999).

Based on the finding that factors involved in HIF-1α mechanism under hypoxic condition such as HIF-1α regulator like PHD2, ubiquitination constitutive enzyme, and CBP have zinc finger motif, the present inventors investigated the effect of CQ, a heavy metal chelator, on HIF-1α mechanism and the effect of TPEN was investigated for comparison.

The present inventors treated human HepG2 hepatoma cells and human SH-SY5Y neuroblastoma cells with CQ and TPEN and investigated HIF-1α activation. As a result, both CQ and TPEN stabilized HIF-1α and thus increased its level under normoxic condition (see FIG. 1). SH-SY5Y neuroblastoma cells were co-treated with CQ and cations ($Zn^{2+}$, $Cu^{2+}$ and $Fe^{2+}$) under normoxic condition. As a result, when CQ was co-treated with $Zn^{2+}$ and $Cu^{2+}$, HIF-1α accumulation was reduced, whereas when CQ was co-treated with $Fe^{2+}$, HIF-1α accumulation was not affected by CQ (see FIG. 2). The present inventors confirmed that CQ derivatives (5-chloroquinolin-8-yl acetate, 5,7-diiodo-8-hydroxyquinoline, 5,7-dibromo-8-hydroxyquinoline and 8-hydroxyquinoline) stabilized HIF-1α in HepG2 and SH-SY5Y cell lines (see FIG. 3). The present inventors further investigated the effect of CQ and TPEN on the activation of VEGF, a target gene of HIF-1α, by RT-PCR. AS a result, CQ induced VEGF expression higher than TPEN did under normoxic condition (see FIG. 4). CQ derivatives (5-chloroquinolin-8-yl acetate, 5,7-diiodo-8-hydroxyquinoline, 5,7-dibromo-8-hydroxyquinoline and 8-hydroxyquinoline) also increased VEGF expression in HepG2 and SH-SY5Y cell lines (see FIG. 5). Then, the inventors investigated the effect of CQ and TPEN on hypoxia-response element (referred as "HRE" hereinafter). As a result, CQ mediated HRE-dependent gene was strongly expressed under normoxic condition (see FIG. 6). The above results indicate that both chelators CQ and TPEN stabilize HIF-1α protein but differ in their effects on transactivation of HIF-1α. In the event, CQ but not TPEN increased expression of VEGF, a target gene of HIF-1α.

The present inventors tested whether CQ changed the activity of PHD2. Particularly, the inventors examined the activity of PHD2 by measuring capture of [$^{35}$S]-labeled VHL (von Hippel-Lindau) by the ODD domain of human HIF-1α protein, since the interaction of VHL with HIF-1α depends on hydroxylation of the proline-402/564 residues. As a result, TPEN but not CQ increased PHD2 activity (see FIG. 7). Thus, zinc chelator TPEN and CQ differed in their effect on PHD2 activity.

HIF-1α is degraded under normoxic condition by ubiquitination. Thus, the present inventors investigated the involvement of CQ and TPEN in HIF-1α ubiquitination. As a result, both CQ and TPEN inhibited HIF-1α ubiquitination under normoxic condition (see FIGS. 8 and 9). HIF-1α is ubiquitinated by the VCB E3 ubiquitin-ligase complex consisting of pVHL, elongin B, elongin C, Cul2, and Rbx 1 (Iwai et al., *Proc Natl Acad Sci USA* 96:12436-12441, 1999; Kamura et al., *Science* 284:657-661, 1999). Rbx 1 has RING-H2-type zinc finger domain (Kamura et al., *Science* 284:657-661, 1999) that plays an important role in activation of ubiquitin-ligase and CQ presumably inhibits the activity (Webster et al., *J Biol Chem* 278:38238-38246, 2003). So, CQ and TPEN increase the level of HIF-1a protein under normoxic condition by inhibiting HIF-1α ubiquitination.

Transactivation of HIF-1α is inhibited by hydroxylation of its asparagine-803 residue catalyzed by FIH-1 (Dann et al., *Proc Natl Acad Sci USA* 99; 15351-15356, 2002; Lando et al., *Science* 295:858-861, 2002). The asparagine-803 hydroxylation of HIF-1α prevents HIF-1α from recruiting its coactivator CBP and thus increases the accumulation of non-functional HIF-1α. That is, transactivation of HIF-1α increases as FIH-1 activity decreases (Freeman et al., *Proc Natl Acad Sci USA* 99:5367-5372, 2002). Based on that, the present inventors investigated the effect of CQ and TPEN on FIH-1 activity. Radiolabeled HIF-1α was loaded alone on resin and as a result it interacted with CBP therein (see FIG. 10A lane 1 and FIG. 10B lane 1). When radiolabeled HIF-1α was reacted with FIH-1, the asparagine-803 of HIF-1α was hydroxylated by FIH-1 and thereby interaction between HIF-1α and its coactivator CBP was inhibited (see FIG. 10A lane 4). When radiolabeled HIF-1α was reacted with FIH-1 in the presence of TPEN, FIH-1 did not prevent HIF-1α from recruiting CBP by hydroxylation, indicating that TPEN did not affect FIH-1 activity to HIF-1α (see FIG. 10B lane 6). When radiolabeled HIF-1α was reacted with CQ, HIF-1α could recruit CBP (see FIG. 10A lanes 2 and 3 and FIG. 10B lane 2). When radiolabeled HIF-1α was reacted with FIH in the presence of CQ, FIH-1 activity to HIF-1α was reduced in a CQ concentration dependent manner (see FIG. 10A lanes 5 and 6 and FIG. 10B lane 5).

The effect of Zn(II) or Cu(II) on the inhibition of FIH-1 activity was investigated. As a result, both Zn(II) and Cu(II) failed to reverse the inhibitory effect of CQ, indicating that Clioquinol inhibits the hydroxylation activity of FIH-1 in a Cu(II)- and Zn(II)-independent manner. The present inventors generated HIF-1α-C($N_{803}$A) mutant by substituting the asparagine-803 residue of HIF-1α with alanine for further experiment. FIH-1 was reacted with radiolabeled HIF-1α-C ($N_{803}$A), followed by investigation of recruitment of CBP to HIF-1α. As a result, CQ or FIH-1 did not change the recruitment of CBP to HIF-1α-C(N803A). The findings suggest that CQ inhibits the hydroxylation of the asparagine-803 of HIF-1α by FIH-1 (see FIG. 12).

The present inventors further investigated FIH-1 activity in the presence of CQ by MALDI-TOF analysis. The result also confirmed that CQ inhibited the hydroxylation of the asparagine-803 of HIF-1α (see FIG. 13).

As shown in the above results, CQ directly reduces FIH-1 activity to HIF-loc. FIH-1 hydroxylates the asparagine-803 residue of HIF-1α and thus prevents HIF-1α transactivation domain from recruiting CBP. In conclusion, CQ interrupts hydroxylation of the asparagine-803 residue of HIF-1α by FIH-1 and thereby increases the accumulation of functional HIF-1α. TPEN did not inhibit FIH-1 activity and thus increased the accumulation of non-functional HIF-1α. CQ did not reduce PHD2 activity but inhibited protein degradation by ubiquitination, and thus increased the accumulation of HIF-1α with hydroxlated proline residue. In addition, CQ inhibits FIH-1 activity and the hydroxylation of the asparagine-803 residue of the accumulated HIF-1α.

The present inventors investigated the effects of CQ and TPEN on hypoxia-induced transactivation by HIF-1α. The interaction between HIF-1α and CBP in the presence of zinc was investigated by co-immunoprecipitation assays and reporter gene assay system. Co-immunoprecipitation assays showed that asparagine-803 non-hydroxylated HIF-1α interacted with its coactivator CBP (see FIG. 14A lane 2), but not in MG132, a protein degradation inhibitor, or TPEN treated cells, indicating that the HIF-1α accumulated upon exposure to MG132 or TPEN differs from that in CQ-treated cells in terms of its ability to interact with CBP (see FIG. 14A lane 1 and FIG. 14B lanes 1 and 3). The present inventors transfected a GAL4-driven reporter plasmid together with HIF-1α linked to the DNA binding domain of the yeast Gal4 protein (GAL4-HIF-1α), followed by investigation of expression of the reporter gene to determine HIF-1α transactivation activity. As expected, CQ increased transactivation activity of HIF-1α under normoxic condition. On the contrary, TPEN did not enhance transactivation activity of HIF-1α under normoxic condition (see FIG. 15). CBP has zinc finger domain CH1 and this CH1 domain binds to HIF-1α. So, the present inventors examined whether the two chelators CQ and TPEN inhibited interaction between HIF-1α and CBP by changing the structure of CH1 domain. From the result of the investigation on the interaction between HIF-1α and CBP in the presence of zinc was confirmed that neither CQ nor TPEN interfered with the interaction between HIF-1α and CBP (see FIG. 16). This result suggests that CQ inhibits FIH-1 and thus increases transactivation activity of HIF-1α and stimulates the interaction between HIF-1α and CBP under normoxic condition.

The present inventors examined the levels of HIF-1α target genes VEGF and EPO in CQ-treated cells by Northern analysis. As a result, CQ induced the expression of both VEGF and EPO under normoxic condition (see FIG. 17).

The present inventors further examined the effect of CQ and its derivatives on angiogenesis. As a result, CQ and its derivatives had VEGF like angiogenesis inducing effect (see FIG. 18).

The present invention provides a therapeutic agent for ischemic disease containing CQ and its derivatives as an active ingredient. The therapeutic agent for ischemic disease targets such diseases as ischemic heart disease, ischemic brain disease and ischemic limb injury.

The present inventors confirmed that CQ induces expressions of VEGF and EPO, and CQ derivatives also induce expression of VEGF. In recent studies, the administration of the recombinant VEGF protein was tried to ischemic disease patients and cardiovascular disease patients (Yoon Y. S., et al., *Mol Cell Biochem* 264:63-74, 2004; Henry T. D., et al., *Circulation* 107:1359-1365, 2003). VEGF expression vector was also administered to ischemic heart disease patients and it was confirmed to be safe (Hedman M. et al., *Circulation* 107: 2677-2683, 2003). VEGF expression contributed to neuroprotection from ischemic brain damage, according to a previous report (Storkebaum E., Lambrechts D., Carmeliet P., *Bioessays* 26:943-954, 2004; Jin K. L., Mao X. O., Greenberg D. A., *Proc Natl Acad Sci USA* 97:10242-10247, 2000; Sun Y., et al., *J Clin Invest* 111:1843-1851, 2003; Zhu W., et al., *Neurosurgery* 57:325-333, 2005). The recombinant EPO protein also exhibited cell protective effect in myocardial infarction and cerebral infarction, according to several reports (Cai Z., et al., *Circulation* 108:79-85, 2003; Ehrenreich H., et al., *Metab Brain Dis* 19:195-206, 2004; Sakanaka M., et al., *Proc Natl Acad Sci USA* 95:4635-4640, 1998; Ehrenreich H., et al., *Mol Med* 8:495-505, 2000). Thus, CQ and its derivatives can be used as a therapeutic agent for ischemic disease by increasing expressions of VEGF and EPO.

CQ and its derivatives of the invention can be applied as it is or in the form of a pharmaceutically acceptable salts. The pharmaceutically acceptable salts of the invention include any pharmaceutically acceptable non-toxic salts which are exemplified by hydrochloric acid, sulfuric acid, nitric acid, phosphoric acid, hydrofluoric acid, hydrobromic acid, formic acid, acetic acid, tartaric acid, lactic acid, citric acid, fumaric acid, maleic acid, succinic acid, methanesulfonic acid, benzensulfonic acid, toluenesulfonic acid, naphthalenesulfonic acid, etc., but not always limited thereto.

The therapeutic agent for ischemic disease of the present invention can be administered singly or treated along with surgical operation, radiotherapy, hormone therapy, chemotherapy and biological reaction regulator, to prevent and treat ischemic disease.

The therapeutic agent for ischemic disease of the present invention can also include, in addition to the above-mentioned active ingredients, one or more pharmaceutically acceptable carriers for the administration. Pharmaceutically acceptable carrier can be selected or be prepared by mixing more than one ingredients selected from a group consisting of saline, sterilized water, Ringer's solution, buffered saline, dextrose solution, maltodextrose solution, glycerol and ethanol. Other general additives such as anti-oxidative agent, buffer solution, bacteriostatic agent, etc, can be added. In order to prepare injectable solutions, pills, capsules, granules or tablets, diluents, dispersing agents, surfactants, binders and lubricants can be additionally added. The composition of the present invention can further be prepared in suitable forms for each disease or according to ingredients by following a method represented in Remington's Pharmaceutical Science (the newest edition), Mack Publishing Company, Easton Pa.

The composition of the present invention can be administered orally or parenterally (for example, intravenous, hypodermic, local or peritoneal injection) The effective dosage of the composition can be determined according to weight, age, gender, health condition, diet, administration frequency, administration method, excretion and severity of a disease. The dosage units can contain, for example, 1, 2, 3 or 4 individual doses or ½, ⅓ or ¼ of an individual dose. An individual dose preferably contains the amount of an active compound which is administered in one application and which usually corresponds to a whole, ½, ⅓ or ¼ of a daily dose.

The effective dosage of the composition of the present invention is 0.5-6 mg/kg, and more preferably 3 mg/kg, and the administration times are 1-3 times a day.

The present invention also provides an angiogenesis inducer containing CQ and its derivatives as an active ingredient.

CQ and its derivatives can be effectively used as an angiogenesis inducer since they have VEGF like angiogenesis inducing effect (see FIG. 18).

The present invention provides a treatment method for ischemic disease containing the step of administering the effective dose of CQ to an ischemia patient.

The ischemic disease herein includes ischemic heart disease, ischemic brain disease, ischemic limb injury, etc. CQ is preferably administered orally or injected intravenously or hypodermically. The dosage for the administration is determined by a doctor in charge. And it is also understood that the effective dose for the treatment is determined by considering age, gender, kind and severity of a disease and other factors. The administration pathway might vary with the conditions of a patient and the severity of a disease.

The present invention also provides a use of CQ and its derivatives for the production of a therapeutic agent for ischemic disease.

The present invention provides a novel use of CQ and its derivatives for the production of a therapeutic agent for ischemic disease by proving that CQ and its derivatives induce transactivation activity of HIF-1α and induce expressions of HIF-1α target genes VEGF and EPO.

DESCRIPTION OF DRAWINGS

The application of the preferred embodiments of the present invention is best understood with reference to the accompanying drawings, wherein.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Effects of CQ, its Derivatives and TPEN on HIF-1α Stabilization

<1-1> Effects of CQ and TPEN on HIF-1α Stabilization in HepG2 Cells

Human HepG2 hepatoma cells (ATCC HB-8065) were cultured under normoxic condition and under hypoxic condition, respectively. HepG2 cells were cultured in MEM (Invitrogen, USA) containing non-essential amino acids and supplemented with 10% FBS (fetal bovine serum: Biowhittaker, USA). The cells were made hypoxic by incubation in anaerobic incubator (Model 1029, Form a Scientific. Inc) at 37° C. with 5% $CO_2$, 10% $H_2$ and 85% $N_2$. The cells were treated with drugs one hour before incubation under hypoxic condition. To separate RNAs, the cells were incubated for 16 hours under hypoxic condition and to separate proteins the cells were cultured for 6 hours under hypoxic condition. The incubated human HepG2 hepatoma cells made normoxic were treated with CQ (Calbiochem, USA) (10, 100, 500 μM) and TPEN (Calbiochem, USA) (5 μM) and other human HepG2 hepatoma cells made hypoxic were treated with CQ (10, 100 μM) and TPEN (5 μM) for 6 hours each. HIF-1α expression was investigated by Western blotting. Samples from each group proceeded to 8% SDS-PAGE for electrophoresis and were then transferred onto nitrocellulose membrane (Schleicher & Schuell Bioscience, USA). Anti-human HIF-1α antibody (BD Pharmingen, USA) (1:800) was used as a primary antibody and mouse-Ig conjugated horseradish peroxidase (1:3,000) was used as a secondary antibody. Anti-β tubulin antibody (BD, Pharmingen, USA) was used as a control.

Figure 1:
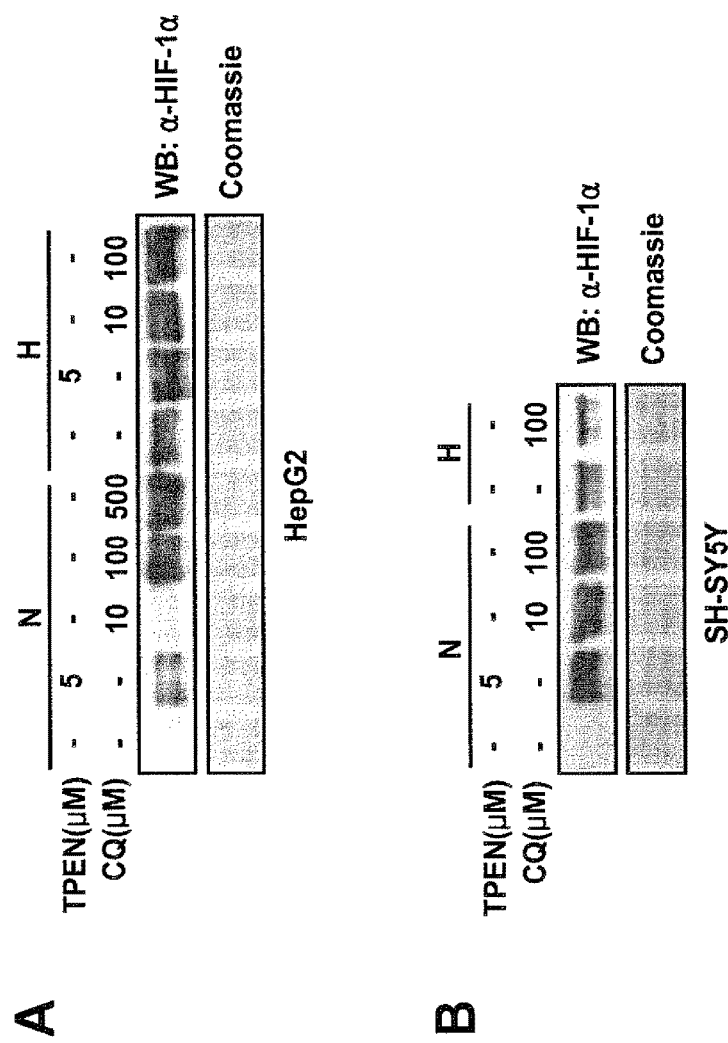
FIG. 1 is a diagram illustrating the expression of HIF-1α (hypoxia-inducible factor-1α) mediated by CQ and TPEN, investigated by Western blotting,
N: normoxia; and
H: hypoxia

As a result, TPEN increased the level of HIF-1α protein in human hepatoma cells under normoxic condition and CQ also strongly induced HIF-1α expression. Both TPEN and CQ induced HIF-1α accumulation under hypoxic condition, compared with a control (FIG. 1A).

<1-2> Effects of CQ and TPEN on HIF-1α Stabilization in SH-SY5Y Cells

Human SH-SY5Y neuroblastoma cells (ATCC CRL-2266) were cultured under normoxic condition and hypoxic condition, respectively. SH-SY5Y cells were cultured in MEM (Invitrogen, USA) containing non-essential amino acids and supplemented with 10% FBS (fetal bovine serum: Biowhittaker, USA). The cells were made hypoxic by incubation in anaerobic incubator (Model 1029, Form a Scientific Inc) at 37° C. with 5% $CO_2$, 10% $H_2$ and 85% $N_2$. The cells were treated with drugs one hour before hypoxic treatment. To separate RNAs, the cells were incubated for 16 hours under hypoxic condition and to separate proteins the cells were cultured for 6 hours under hypoxic condition. The normoxic human SH-SY5Y neuroblastoma cells were treated with TPEN (5 μM) and CQ (10, 100 μM), while hypoxic human SH-SY5Y neuroblastoma cells were treated with CQ (100 μM), for 6 hours each. HIF-1α expression was investigated by Western blotting. Samples from each group proceeded to 8% SDS-PAGE for electrophoresis and were then transferred onto nitrocellulose membrane (Sigma, USA). Anti-human HIF-1α antibody (BD, Pharmingen, USA) (1:800) was used as a primary antibody and mouse-Ig conjugated horseradish:peroxidase (1:3,000) was used as a secondary antibody. Anti-β tubulin antibody (BD, Pharmingen, USA) was used as a control.

As a result, TPEN increased the level of HIF-1α protein in human neuroblastoma cells and CQ also strongly induced HIF-1α accumulation. All of the control, TPEN and CQ induced HIF-1α accumulation (FIG. 1B).

<1-3> Effects of CQ and Cation on HIF-1α Stabilization in SH-SY5Y Cells

Human SH-SY5Y neuroblastoma cells were cultured under normoxic and hypoxic conditions by the same manner as described in Example <1-2>. After culturing, human SH-SY5Y neuroblastoma cells were treated with CQ (50 μM) under normoxic condition, together with $Zn^{2+}$ (10 μM), $Cu^{2+}$ (10 μM) and $Fe^{2+}$ (10 μM) respectively, followed by further culture for 16 hours. Western blotting was performed by the same manner as described in Example <1-2> to examine HIF-1α expression.

Figure 2:
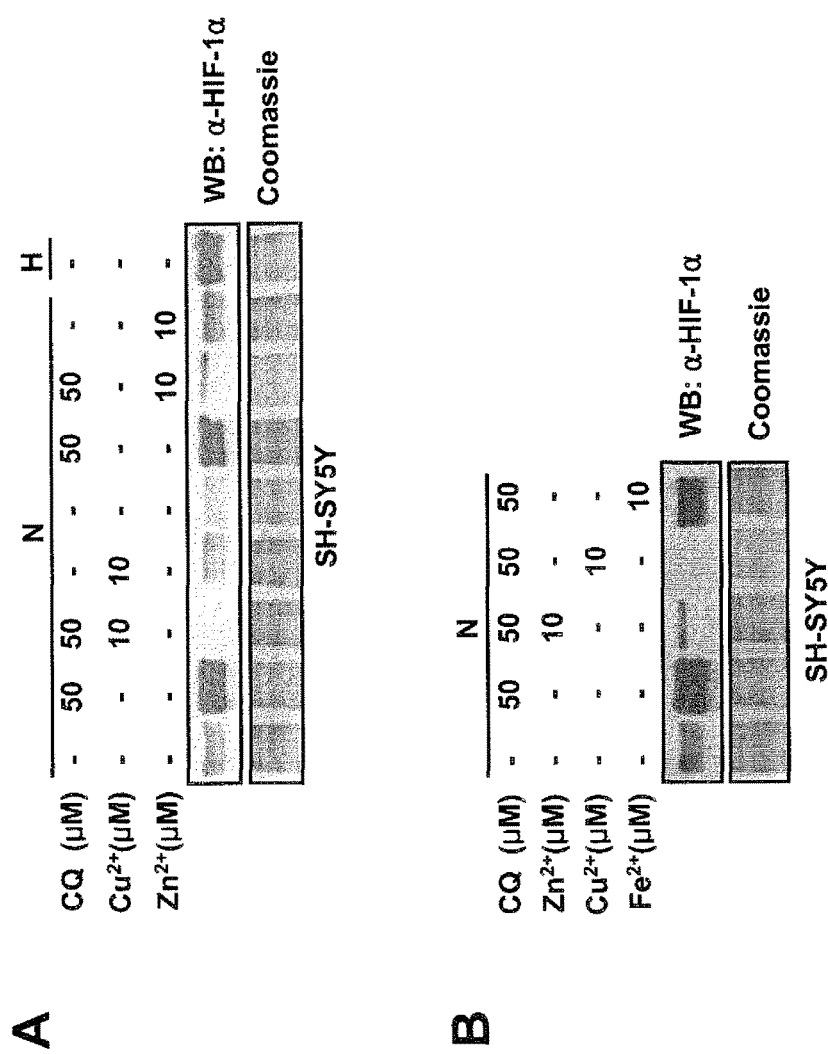
FIG. 2 is a diagram illustrating the expression of HIF-1α mediated by CQ and cation, investigated by Western blotting,
N: normoxia; and
H: hypoxia

As a result, the addition of Zn(II) and Cu(II) reversed the effect of CQ, indicating that it stabilizes HIF-1α by depleting Zn(II) and Cu(II) (FIG. 2A). The addition of Fe(IIu) failed to reverse the effect of CQ (FIG. 2B), indicating that Fe(II) is not involved in HIF-1α stabilization by CQ.

<1-4> Effect of CQ Derivatives on HIF-1α Stabilization in HepG2 and SH-SY5Y Cells The present inventors investigated the effect of CQ derivatives (5-chloroquinolin-8-yl acetate, 5,7-diiodo-8-hydroxyquinoline, 5,7-dibromo-8-hydroxyquinoline and 8-hydroxyquinoline) on HIF-1α stabilization in HepG2 and SH-SY5Y cells by the same manner as described in Examples <1-1> and <1-2>. Particularly, HepG2 and SH-SY5Y cells were cultured as described in Examples <1-1> and <1-2> and then treated with CQ and CQ derivatives at the concentrations of 5, 10, 50 and 100 μM. Western blotting was performed by the same manner as described in Examples <1-1> and <1-2>. Anti-HSP70 antibody (Stressgen, Canada) was used for a control.

Figure 3:
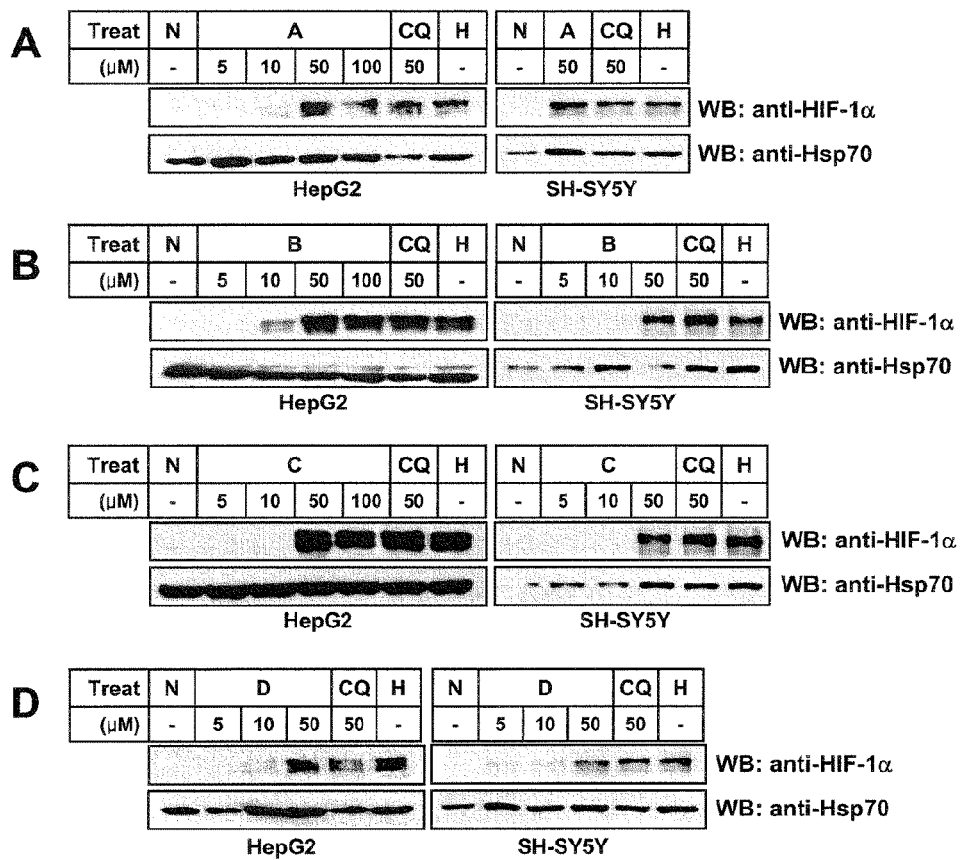
FIG. 3 is a diagram illustrating the expression of HIF-1α (hypoxia-inducible factor-1α) mediated by CQ and its derivatives, investigated by Western blotting,
N: normoxia;
H: hypoxia;
A: 5-chloroquinolin-8-yl acetate;
B: 5,7-diiodo-8-hydroxyquinoline;
C: 5,7-dibromo-8-hydroxyquinoline; and
D: 8-hydroxyquinoline

As a result, CQ derivatives (5-chloroquinolin-8-yl acetate, 5,7-diiodo-8-hydroxyquinoline, 5,7-dibromo-8-hydroxyquinoline and 8-hydroxyquinoline), like CQ, induced HIF-1α stabilization (FIG. 3).

<1-5> Effects of CQ and TPEN on the Expression of VEGF, a HIF-1α Target Gene

Human SH-SY5Y neuroblastoma cells and human HepG2 hepatoma cells were cultured under normoxic and hypoxic conditions as described in Examples <1-1> and <1-2>. After culturing under normoxic condition, human SH-SY5Y neuroblastoma cells and human HepG2 hepatoma cells were treated with TPEN (5 μM) and CQ (10, 100 μM). The cells cultured under hypoxic condition were treated with TPEN (5 μM) and CQ (100 μM) for 16 hours. Total RNA was extracted by using RNase Spin column (Qiagen, USA). cDNA was synthesized from 1 μg of the extracted RNA using AMV reverse transcriptase (Promega, USA) and random hexamer (Gibco-BRL, USA). RT-PCR was performed using the synthesized cDNA as a template with a VEGF forward primer represented by SEQ. ID. NO: 1 (5'-ccatgaactttctgctgtctt-3') and a VEGF reverse primer represented by SEQ. ID. NO: 2 (5'-atcgcatcaggggcacacag-3'). RT-PCR conditions were as follows; predenaturation at 95° C. for 5 minutes, denaturation at 95° C. for 45 seconds, annealing at 56° C. for 45 seconds, polymerization at 72° C. for 60 seconds, 30 cycles from denaturation to polymerization. For the control, RT-PCR was performed again with an 18S forward primer represented by SEQ. ID. NO: 3 (5'-accgcagctaggaataatggaata-3') and an 18S reverse primer represented by SEQ. ID. NO: 4 (5'-ctttcgctctg-gtccgtctt-3'). RT-PCR conditions were as follows; predenaturation at 95° C. for 5 minutes, denaturation at 95° C. for 45 seconds, annealing at 56° C. for 45 seconds, polymerization at 72° C. for 60 seconds, 30 cycles from denaturation to polymerization.

Figure 4:
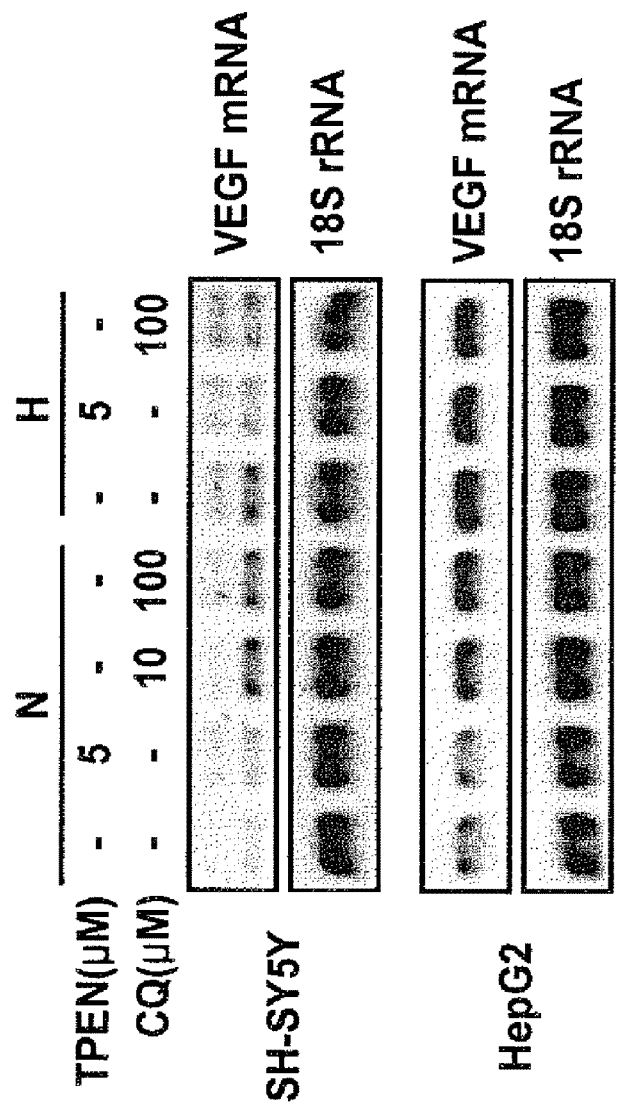
FIG. 4 is a diagram illustrating the expression of VEGF mediated by CQ and TPEN, investigated by RT-PCR,
N: normoxia; and
H: hypoxia

As a result, CQ and TPEN differed in their effects on VEGF expression in human SH-SY5Y neuroblastoma cells under normoxic condition. CQ increased VEGF expression under normoxic condition, while TPEN reduced VEGF expression. CQ and TPEN differed in their effects on VEGF expression in human HepG2 hepatoma cells too. But under hypoxic condition, none of the control, TPEN and CQ increased VEGF expression (FIG. 4).

<1-6> Effects of CQ Derivatives on the Expression of VEGF, a HIF-1α Target Gene

Human HepG2 cells and SH-SY5Y cells were cultured as described in Examples <1-1> and <1-2>. The cells were treated with CQ and CQ derivatives (5-chloroquinolin-8-yl acetate, 5,7-diiodo-8-hydroxyquinoline, 5,7-dibromo-8-hydroxyquinoline and 8-hydroxyquinoline) at the concentrations of 5, 10, 50 and 100 μM and RT-PCR was performed as described in Example <1-5>.

Figure 5:
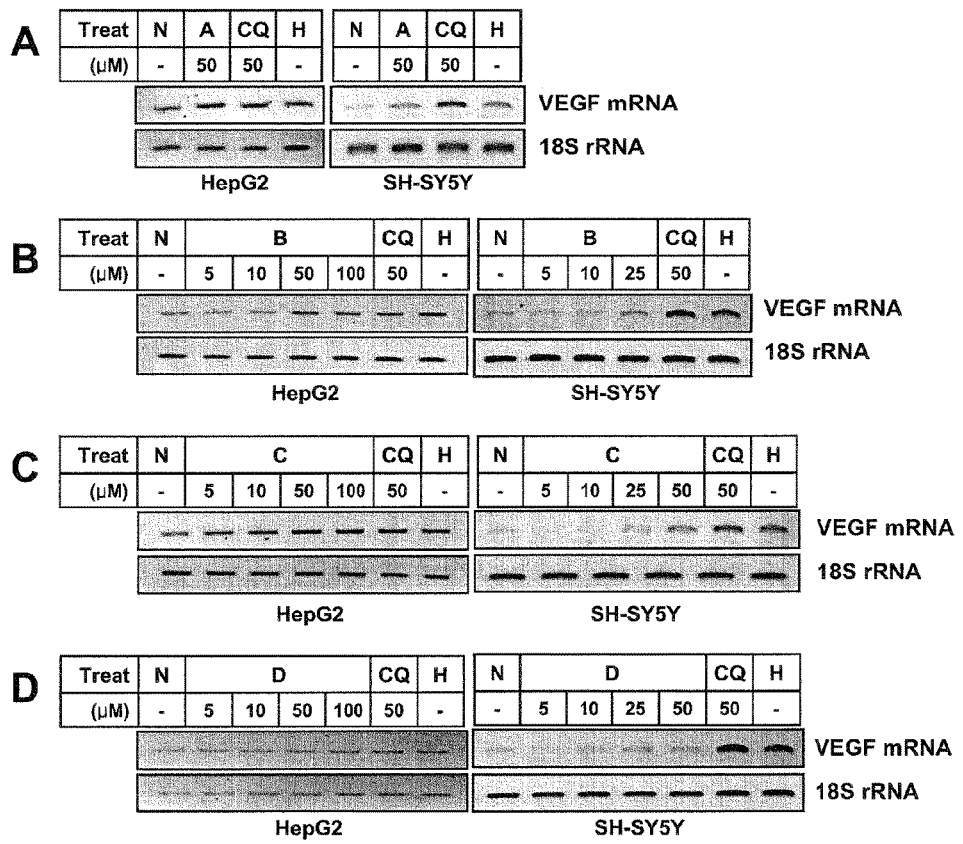
FIG. 5 is a diagram illustrating the expression of VEGF mediated by CQ and its derivatives, investigated by RT-PCR,
N: normoxia;
H: hypoxia;
A: 5-chloroquinolin-8-yl acetate;
B: 5,7-diiodo-8-hydroxyquinoline;
C: 5,7-dibromo-8-hydroxyquinoline; and
D: 8-hydroxyquinoline

As a result, CQ derivatives did not increase VEGF expression in HepG2 cells, compared with what CQ did in SH-SY5Y cells under hypoxic condition. In the meantime, such CQ derivatives as 5-chloroquinolin-8-yl acetate (50 μM), 5,7-diiodo-8-hydroxyquinoline (25 μM) and 8-hydroxyquinoline (50 μM) increased VEGF expression 40-50% to the expression level induced by CQ and another CQ derivative 5,7-dibromo-8-hydroxyquinoline (50 μM) increased VEGF expression 60-70% to the expression level induced by CQ (FIG. 5).

<1-7> Effects of CQ and TPEN on HRE (Hypoxia-Response Element) Dependent Gene Expression in HepG2 Hepatoma Cells Human HepG2 hepatoma cells were grown to the density of 5×10$^4$ and then transfected with 100 ng of HRE-driven reporter plasmid, p(HRE)$_4$-luc together with plasmid pCHO110 which encodes β-galactosidase. The transfected human HepG2 hepatoma cells were cultured under normoxic condition and hypoxic condition and then treated with TPEN (5, 10 µM) and CQ (10, 50 µM) for 16 hours each. 48 hours after the transfection, luciferase activities were analyzed using the reporter gene assay system (Promega, USA) and normalized by β-galactosidase activities.

Figure 6:
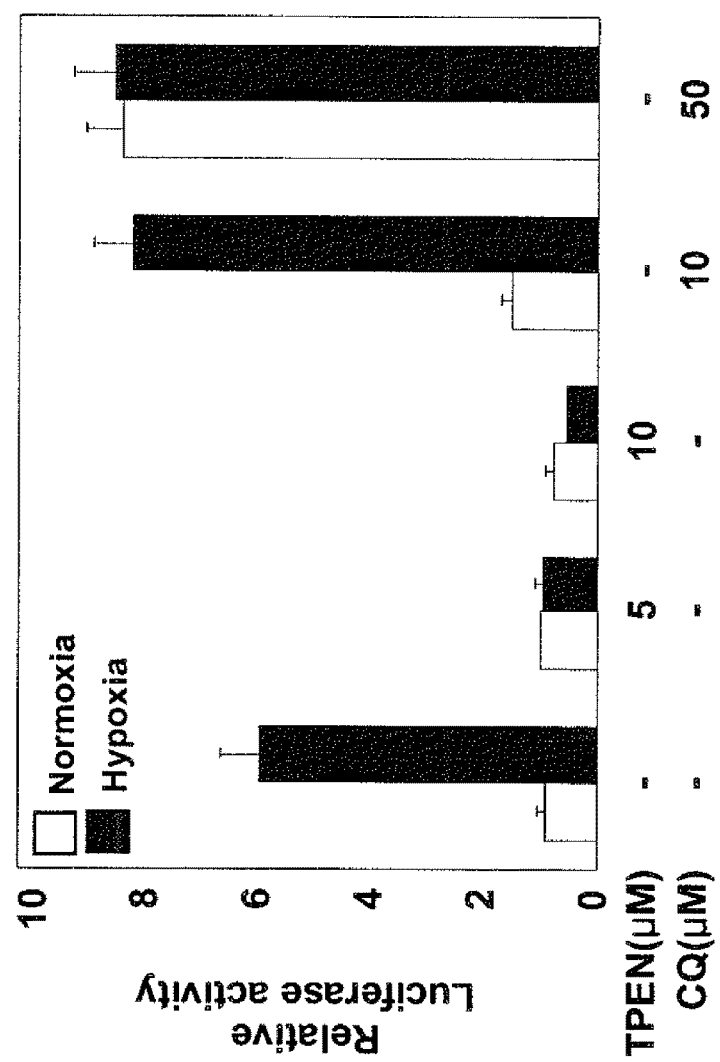
FIG. 6 is a diagram illustrating the HRE dependent gene expression mediated by CQ and TPEN, investigated by reporter gene assay system.

As a result, CQ but not TPEN induced HIF-1α dependent hypoxia-response element (HRE) activity (FIG. 6).

EXAMPLE 2

Effects of CQ and TPEN on the Activity of PHD2

The present inventors investigated the effect of CQ on the activity of PHD2. Human PHD2 gene (AJ310543) was cloned into pET21b His2(+) vector and then the human PHD2 was expressed with a histidine tag in *E. coli* and purified by Ni-affinity chromatography (Choi, K. O. et al., *Mol. Pharmacol.* 68, 1803-1809, 2005). The in vitro VHL pull down assay was performed as described by Haakkola et al (Haakkola, P. et al., *Science* 292,468-472, 2001). Particularly, [$^{35}$S]-methionine-labeled VHL protein was synthesized by in vitro transcription and translation using the pcDNA3.1/myc-hygro-VHL plasmid (Promega, Cat# L1170, USA), according to the instruction manual (Promega, Cat# L1170). GST-ODD (amino acids 401-603 of human HIF-1α) was expressed in *E. coli* and purified with glutathione-uniflow resin according to the instruction manual (BD Bioscience Clontech, Cat# 8912-1, USA). Resin-bound GST-ODD (200 µg protein/about 80 µl of resin volume) was incubated in the presence of 2 mM ascorbic acid, 100 µM FeCl$_2$ and 5 mM α a-ketoglutarate with 1.5-3 µg of PHD2 in 200 µl of NETN buffer (200 mM Tris (pH 8.0), 100 mM NaCl, 1 mM EDTA, 0.5% Nonidet P-40, 1 mM PMSF) with mild agitation for 90 minutes at 30° C. The reaction mixture was centrifuged with 500×g for 2 minutes and washed three times with 10 volumes of NETN buffer. Resin-bound ODD was mixed with 10 µM [$^{35}$S]-labeled VHL in 50 µl of EBC buffer (120 mM NaCl, 50 mM Tris-HCl(pH8.0), 0.5% (v/v) Nonidet P-40). After agitation at 4° C. for 2 hours, the resin was washed three times with 1 ml of NETN buffer, and proteins were eluted in 3×SDS sample buffer, fractionated by 12% SDS-PAGE, and detected by autoradiography. The amount of each sample loaded was monitored by staining the GST-ODD with Coomassie blue.

Figure 7:
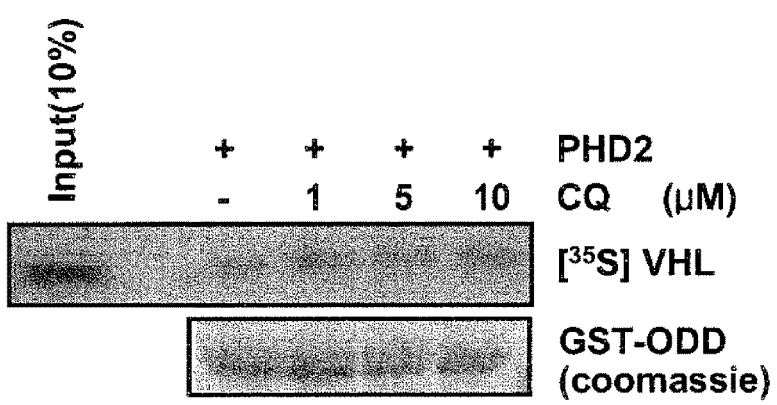
FIG. 7 is a diagram illustrating the effects of CQ and TPEN on PHD2 activation.
Figure 7:
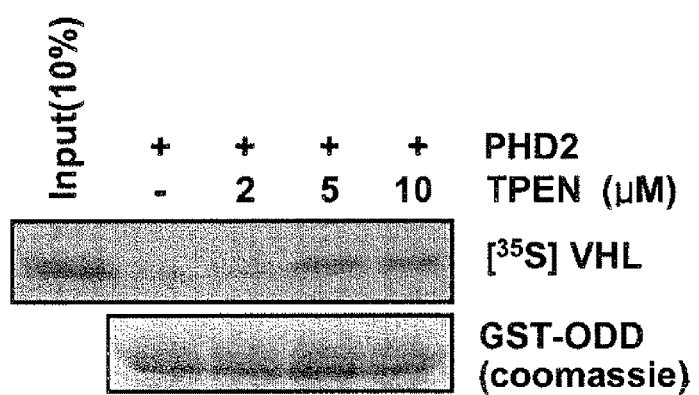

As a result, TPEN but not CQ increased the activity of PHD2 (FIG. 7).

EXAMPLE 3

Effects of CQ and TPEN on HIF-1α Ubiquitination

<3-1> In Vitro Ubiquitination

HeLa cells were cultured in DMEM (Invitrogen, USA) supplemented with 10% FBS (fetal bovine serum: Biowhittaker, USA). When HeLa cells were grown to 80% confluence on 100-mm tissue culture plates, the cells were washed twice with cold hypotonic extraction buffer (20 mM Tris-HCl (pH 7.5), 5 mM KCl, 1.5 mM MgCl$_2$, 1 mM dithiothreitol, 2 µg/ml aprotinin, 2 µg/ml leupeptin, 0.2 mM PMSF). After removing the buffer, the cells were disrupted in a Dounce homogenizer and the crude extract was centrifuged at 10,000×g for 10 minutes at 4° C. to remove cell debris and nuclei. Aliquots of the supernatant (S-10 fraction) were stored at −70° C. Ubiquitination assays were carried out at 30° C. for 270 minutes in a total volume of 40 µl containing 2 µl of [$^{35}$S]-labeled human HIF-1α-programmed reticulocyte lysate, 27 µl of S-10 extract, 4 µl of 10×ATP-regenerating system (20 mM Tris (pH 7.5), 10 mM ATP, 10 mM magnesium acetate, 300 mM creatine phosphate, 0.5 µg/ml creatine phospholinase), 4 µl of 5 mg/ml ubiquitin (Sigma, USA) and 0.83 µl of 150 µM ubiquitin aldehyde (Sigma, USA). In the meantime, another same was treated with 100 µM of CQ. SDA sample buffer was added and the reaction products were analyzed by 6% SDS-PAGE and autoradiography (Cockman et al., *J Biol Chem* 275:25733-25741, 2000).

Figure 8:
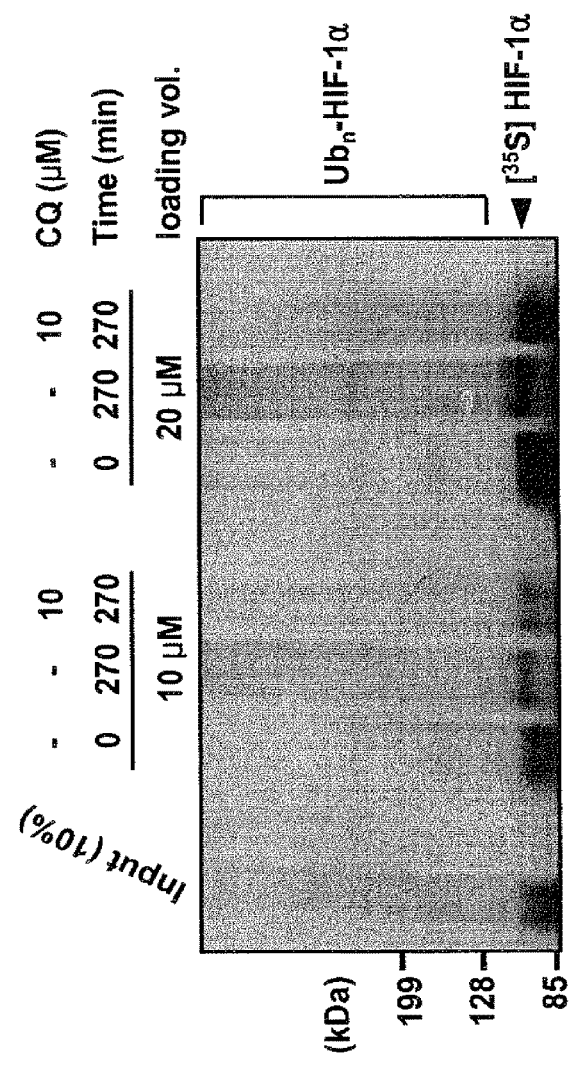
FIG. 8 is a diagram illustrating the in vitro HIF-1α ubiquitination by CQ.
Figure 9:
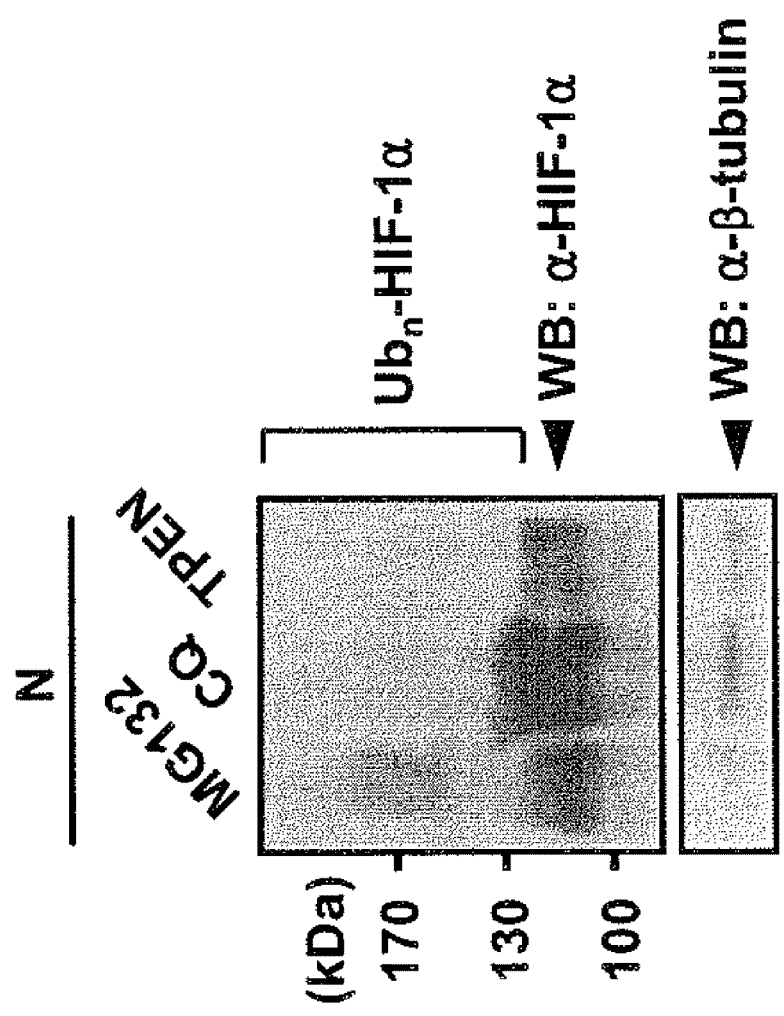
FIG. 9 is a diagram illustrating the in vivo HIF-1α ubiquitination by CQ and TPEN.

As a result, CQ was confirmed to inhibit HIF-1α ubiquitination (FIG. 8).

<3-2> In Vivo Ubiquitination

Human HepG2 hepatoma cells were treated with TPEN (5 µM), CQ (100 µM) and MG132 (5 µM) for 6 hours under normoxic condition. Western blotting was carried out to detect HIF-1α ubiquitination, by the same manner as described in Example <1-2>.

MG132 specifically inhibits the 26S proteasome and thereby reduces the degradation of ubiquitin-conjugated HIF-1α even in normoxic condition. From the experiment, it was confirmed that CQ blocks the ubiquitination of HIF-1α, causing it to accumulate in normoxic cells in agreement with the results of the in vitro ubiquitination assay in Example <3-1> (FIG. 8).

EXAMPLE 4

Effects of CQ and TPEN on FIH-1

Transactivation of HIF-11 is inhibited by hydroxylation of its asparagine-803 residue by FIH-1 (Dann et al., *Proc Natl Acad Sci USA* 99, 15351-15356, 2002; Lando et al., *Science* 295:858-861, 2002). The hydroxylation of the asparagine-803 residue of HIF-1α prevents HIF-1α from recruiting its co-activator CBP. The activity of HIF-1α increases as the activity of FIH-1 decreases (Freeman et al., *Proc Natl Acad Sci USA* 99:5367-5372, 2002). Thus, the present inventors investigated the effects of CQ and TPEN on FIH-1 activity. The effect of the co-treatment of CQ with Zn(II) or Cu(II) on FIH-1 activity was also investigated as described in Example <1-3>.

<4-1> In Vitro FIH-1 Activity

The human FIH-1 gene (AF395830) was cloned into pET28a vector (Novagen, USA) and FIH-1 was overexpressed in *E. coli* as a histidine-tagged fusion protein and purified by Ni-affinity chromatography. The fusion protein was purified by gel-filtration chromatography (Hi-Load Superdex 200) and concentrated by ultrafiltration (Choi et al., *Mol Pharmacol* 68:1803-1809, 2005).

20 µl of [$^{35}$S]-labeled human HIF-1α protein was reacted with the purified FIH-1 protein in a reaction buffer (200 µl; 20 mM Tris-HCl (pH 7.5), 5 mM KCl, 1.5 mM MgCl$_2$, 1 mM DTT, 2 mM ascorbic acid, 2 mM α-ketoglutarate, 250 µM FeSO$_4$) for one hour at 30° C. The resin-bound GST-CBP N-domain (amino acids 1-450) (Kamei et al., *Cell* 85:403-414, 1996) was then added to 1 µg of each mixture in 500 µl of binding buffer (200 mM Tris-HCl (pH 8.0), 150 mM NaCl, 20 µM ZnCl$_2$, 0.5 mM DTT) and incubation continued for one hour at 4° C. Glutathione-uniflow resin bound protein was washed four times with 1 ml of 0.1% Nondiet P-40 containing binding buffer, and visualized by SDS-PAGE by eluting using SDS sample buffer (Dann et al., *Proc Natl Acad Sci USA* 99:15351-15356, 2002). The present inventors substituted the asparagine-803 residue of HIF-1α with alanine to generate HIF-1α mutant [HIF-1α-C(N803A)], followed by investigation on FIH-1 activity by the same manner as described above.

Radio-labeled HIF-1α was reacted with the purified recombinant FIH-1, in the presence or absence of CQ or TPEN. FIH-1 was expected to hydrolyze the asparagine-803 residue of HIF-1α and thus inhibit the interaction with CBP binding to HIF-1α transactivation domain (Mahon, P. C. et al., *Genes Dev.* 15, 2675-2686, 2001; Dannm C. E. R., et al., *Proc. Natl. Acad. Sci. USA* 99, 15351-15356, 2002; Lando, D., et al., *Science* 295, 858-861, 2002; Freedman, S. J. et al., *Proc. Natl. Acad. Sci. USA* 99, 5367-5372, 2002).

Figure 10:
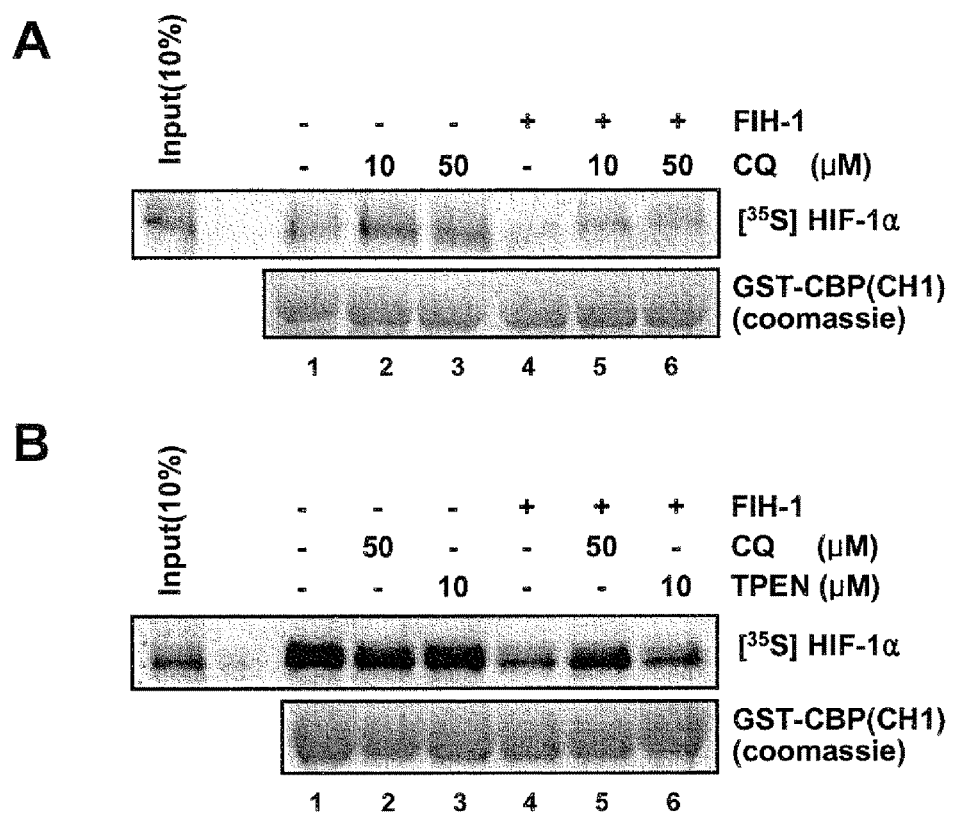
FIG. 10 is a diagram illustrating the effects of CQ and TPEN on FIH-1 activity.

As a result, the radio-labeled HIF-1α interacted with bead-bound GST-CBP, and the addition of FIH-1 reduced significantly the interaction between HIF-1α and CBP (FIG. 10A lanes 1 and 4, and FIG. 10B lanes 1 and 4). FIH-1 hydrolyzed the asparagine-803 residue of HIF-1α and thereby reduced the interaction between HIF-1α transactivation domain and CBP. In conclusion, FIH-1 activation inhibited the interaction between HIF-1α and CBP. The present inventors investigated the effect of CQ on FIH-1 activity. FIH-1 activity was reduced in the presence of CQ (10 μM and 50 μM), and thereby the interaction between HIF-1α and CBP was increased (FIG. 10A lanes 5 and 6, FIG. 10B lane 5, FIG. 11A lane 4 and FIG. 11B lane 4). In the meantime, TPEN did not reduce FIH-1 activity (FIG. 10B Lanes 3 and 6).

Figure 11:
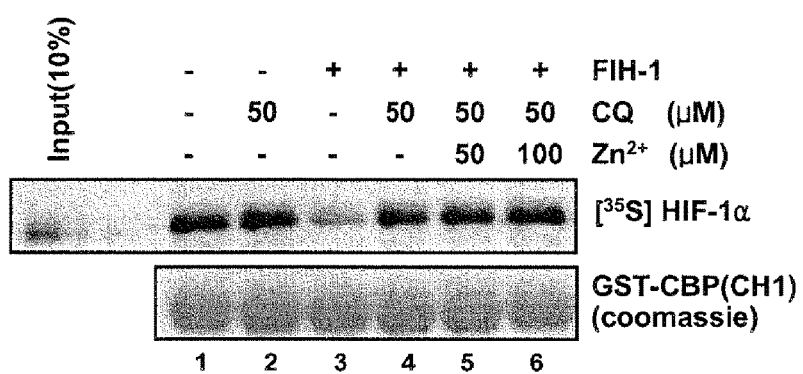
FIG. 11 is a diagram illustrating the effects of CQ and cation on FIH-1 activity.
Figure 11:
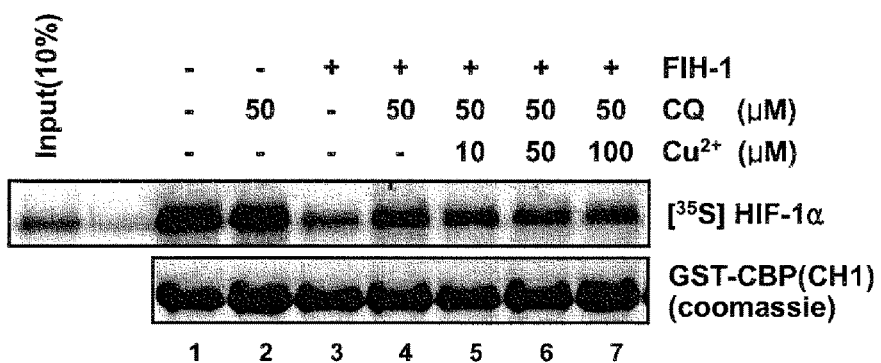

The present inventors also investigated the effect of Zn(II) or Cu(II) on the inhibition of FIH-1 activity. As a result, neither Zn(II) nor Cu(II) could reverse the FIH-1 activity inhibition effect (FIG. 11).

Figure 12:
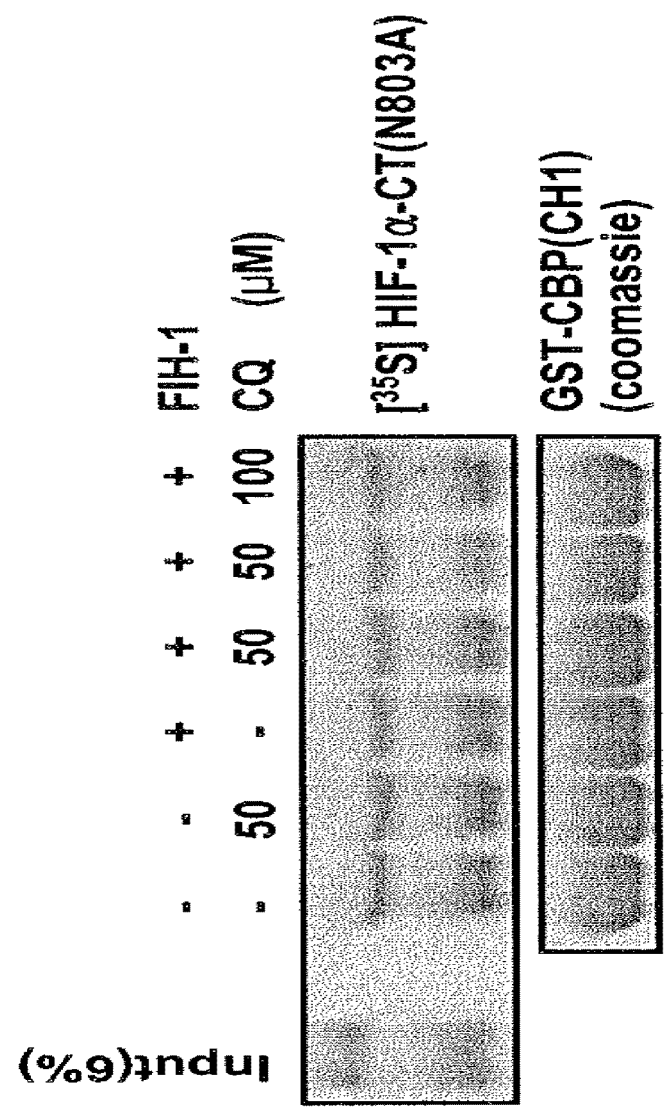
FIG. 12 is a diagram illustrating the effect of CQ on FIH-1 activity in HIF-1α mutant.

HIF-1α-C(N803A) mutant was generated by substituting the asparagine-803 residue of HIF-1α with alanine. FIH-1 and HIF-1α-C (N803A) were reacted together to examine the interaction with CBP. As a result, the presence or absence of CQ or FIH-1 did not change the interaction between CBP and HIF-1α-C (N803A). This result indicates that CQ inhibits the effect of FIH-1 on the hydroxylation of the asparagine-803 of HIF-1α (FIG. 12).

<4-2> Effect of CQ on FIH-1 Activity by Using MALDI-TOF

The present inventors examined FIH-1 activity by measuring the asparagine hydroxylation of F-HIF-1α peptide. The peptide hydroxylation was measured by mass spectrophotometry.

Particularly, F-HIF-1α (788-822 amino acids: FITC-aca-DESGLPQLTSYDCEVNAPIQGSRNLLQGEELLRAL) containing fluorescein and aca (aminocaproic acid) linker (AnyGen, KwangJu, Korea) at N-terminal was reacted with FIH-1 protein. The F-HIF-1α peptide was incubated at a final concentration of 4 μM with 2.8 μg of recombinant FIH-1 in reaction solution [20 mM Tris buffer (pH 7.5), 5 mM KCl, 1.5 mM $MgCl_2$, 100 μM α-ketoglutarate and 400 μM ascorbic acid: final volume 50 μl]. After incubation with agitation for 2 hours at room temperature, excess salts were removed with $ZipTip_{C18}$ (Millipore, USA). The F-HIF-1α peptide was eluted from the tip with a-cyano-4-hydroxycinnamic acid in acetonitrile/water (50:50 v/v) containing 0.1% TFA followed by washing with distilled water containing 0.1% TFA. The eluted peptide solution was transferred to a MALDI sample plate and MALDI-TOF measurements were performed with a Voyager analyzer (Applied Biosystems, USA).

Figure 13:
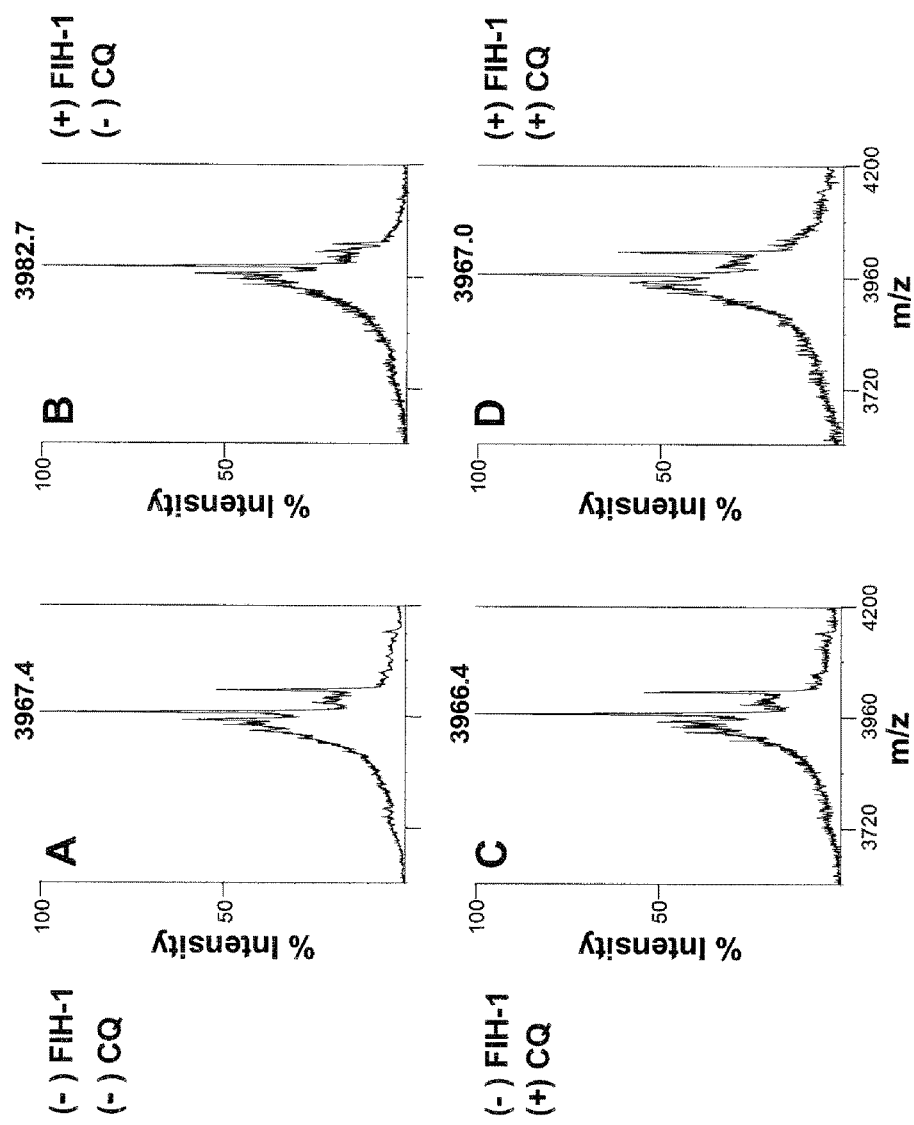
FIG. 13 is a diagram illustrating the effect of CQ on FIH-1 activity measured by MALDI-TOF analysis.

As a result, after treatment with FIH-1 the peptide gave a new MALDI-TOF peak corresponding to an increase of molecular weight of 16 (FIGS. 13A and 13B). This result confirms that the recombinant FIH-1 hydroxylates aspar-agine-803 of HIF-1α. In contrast, when the peptide was incubated with FIH-1 and CQ, its molecular weight did not increase (FIGS. 13C and 13D). This observation confirms that CQ inhibits the asparagine-hydroxylating activity of FIH-1.

EXAMPLE 5

Effects of CQ and TPEN on Hypoxia-Induced Transactivation by HIF-1α

<5-1> Investigation of the Effects of CQ and TPEN by co-Immunoprecipitation

Human HepG2 hepatoma cells were grown to 80% confluence on 100-mm tissue culture plates and treated with MG132 (5 μM) for 6 hours in normoxic condition. The cells were treated with 100 μM of CQ in normoxic condition. Total cell extract was prepared by the method of Jaakkola, et al (Jaakkola et al., *Science* 292:468-472, 2001). For immunoprecipitation, 200 μg of samples of whole cell lysates were reacted with 1 μg of anti-mouse IgG (Santa Cruz Biotechnology, USA) and 10 μl of 0.5% ImmunoPure immobilized protein A/G gel (Pierce, USA) for 30 minutes at 4° C. After removing protein A/G gel, the cleared extracts were mixed with 1 μg of anti-CBP antibody (Santa Cruz Biotechnology, USA). After addition of 15 μl of 0.5% ImmunoPure immobilized protein A/G gel, they were left at 4° C. for 16 hours. The immunoprecipitates were pelleted, washed four times with PBS and resuspended in SDS sample buffer. Samples were then boiled for 5 minutes and run on 8% SDS-polyacrylamide gels, and the proteins were transferred to nitrocellulose membranes by semi-dry transfer (Trans-Blot SD, Bio-Red, Hercules, USA). Co-immunoprecipitated proteins were reacted with anti-human HIF-1α antibody (BD, Pharmingen, USA) and/or anti-CBP antibody and visualized by enhanced chemiluminescence, according to the manufacturer's instruction (Amersham, USA), with anti-mouse or anti-rabbit Ig conjugated with horseradish peroxidase (HRP) as a secondary antibody.

Figure 14:
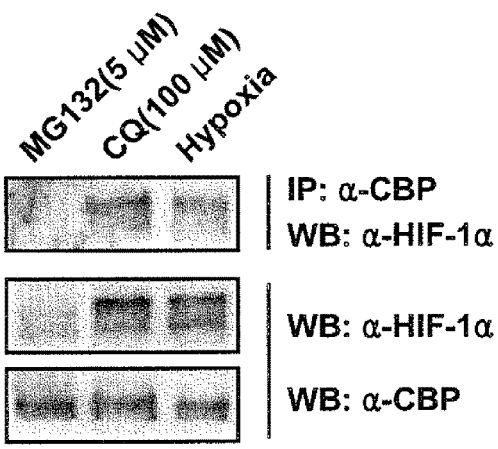
FIG. 14 is a diagram illustrating the in vivo recruitment of CBP to HIF-1α by CQ, investigated by co-immunoprecipitation.
Figure 14:
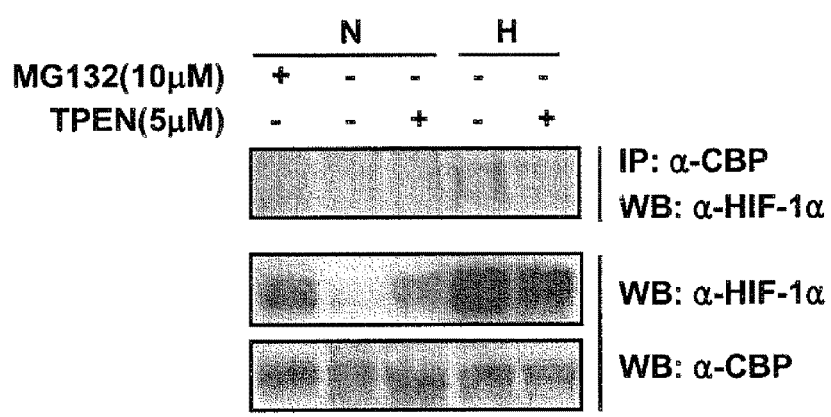

As a result, HIF-1α interacted with CBP in both CQ-treated cells and hypoxic cells but not in MG132 treated cells (FIG. 14A). MG132 inhibited 26S proteasome specifically, and thus inhibited the degradation of ubiquitin-conjugated HIF-1α even in normoxic condition. FIH-1 induced hydroxylation of the asparagine-803 residue of HIF-1α in MG132-treated cells, indicating that interaction between HIF-1α and CBP was inhibited. TPEN also inhibited the interaction between HIF-1α and CBP (FIG. 14).

<5-2> Investigation of the Effects of CQ and TPEN by Using Reporter Gene Assay System Human HepG2 hepatoma cells were cultured at the concentration of $5 \times 10^4$, which were transfected with 100 ng of Gal-4-driven reporter plasmid encoding the firefly luciferase gene under the control of the Gal4 binding site together with pGal4/HIF-1α plasmid which expresses HIF-1α linked to the DNA binding domain of the yeast Gal4 protein (amino acids 1-147). The transfected human HepG2 hepatoma cells were incubated in both normoxic and hypoxic conditions and then treated with CQ (10, 50 μM) for 16 hours in normoxic condition. 48 hours after the transfection, luciferase activities were analyzed using the reporter gene assay system (Promega, USA) and normalized by β-galactosidase activities. The human HepG2 hepatoma cells were treated with TPEN (5 μM) in both normoxic and hypoxic conditions 16 hours prior to harvest.

Figure 15:
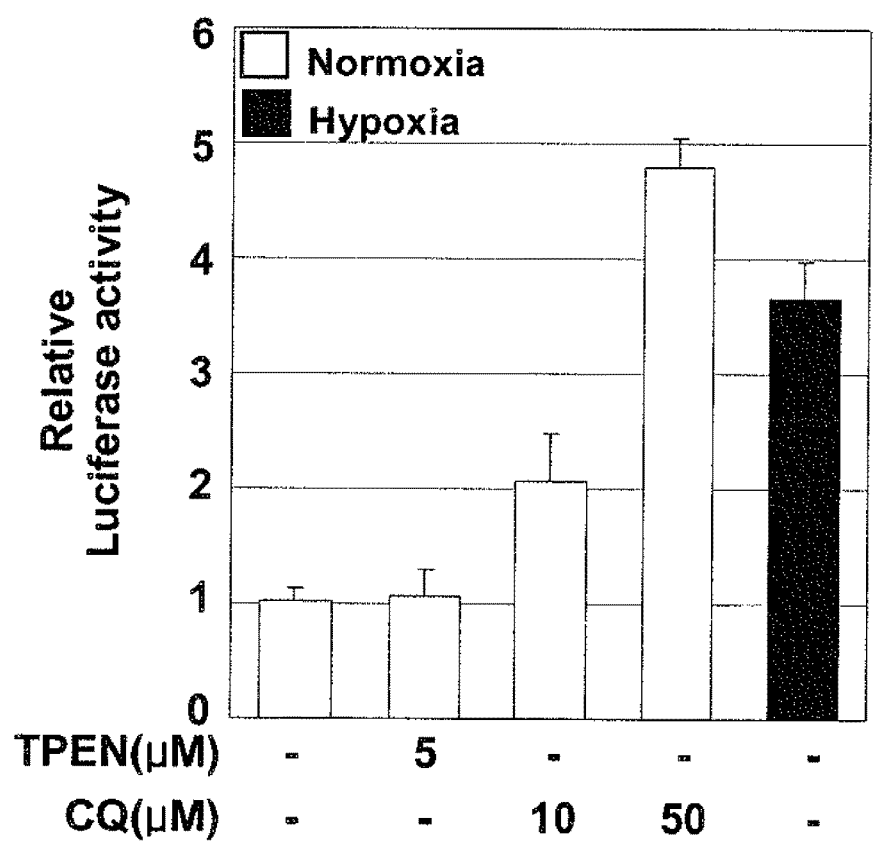
FIG. 15 is a diagram illustrating the effects of CQ and TPEN on hypoxia-induced transactivation by HIF-1α, investigated by reporter gene assay system.

Gal4 fusion protein was able to bind to Gal4 binding site, and the reporter gene could only be transcribed when HIF-1α had transactivation activity. CQ increased transactivation activity of HIF-1α in normoxic condition. In contrast, TPEN increased HIF-1α activity in hypoxic condition but not in normoxic condition (FIG. 15).

<5-3> Effects of CQ and TPEN on In Vitro Interaction between HIF-1α and CBP

20 μl of [$^{35}$S]-labeled human HIF-1α protein was reacted with bead-bound GST-CBP N-domain (amino acids 1-450) (Kawei et al., Cell 85:403-413, 1996) at 4° C. for 1 hour with or without ZnCl$_2$ (20 μM) in a reaction buffer (200 μl; 20 mM Tris-HCl(pH 7.5), 5 mM KCl, 1.5 mM MgCl$_2$, 1 mM DTT). Glutathione-uniflow resin bound protein was washed four times with 1 ml of 0.1% Nonidet P-40 containing binding buffer, eluted by heating in SDS sample buffer, and fractionated by SDS-PAGE (Dann et al., Proc Natl Acad Sci USA 99:15351-15356, 2002).

Figure 16:
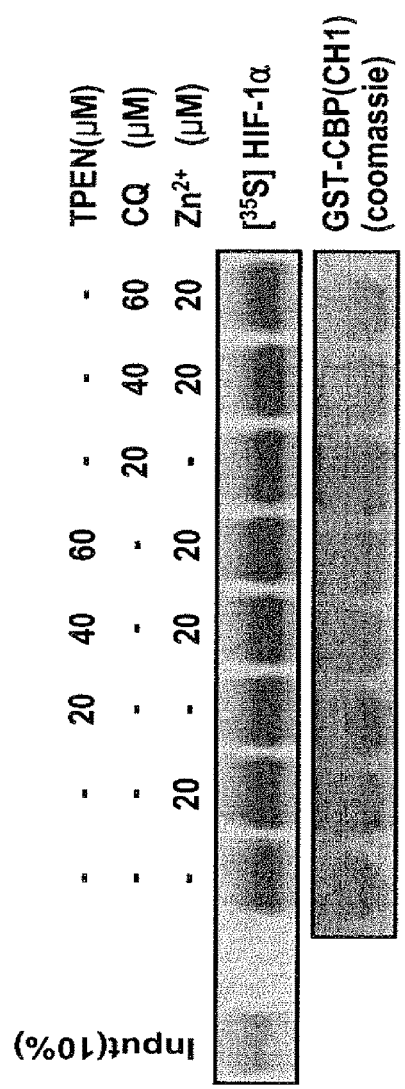
FIG. 16 is a diagram illustrating the effects of CQ and TPEN on in vitro interaction between HIF-1α and CBP.

As a result, although the zinc finger CH1 domain was located in the HIF-1α-interacting region of CBP, neither CQ nor TPEN directly affected the interaction between CBP and HIF-1α (FIG. 16).

EXAMPLE 6

Effects of CQ on the Expressions of HIF-1α Target Genes VEGF and EPO

Human HepG2 hepatoma cells and SH-SY5Y neuroblastoma cells were treated with CQ (10, 50 μM) and then cultured for 16 hours in normoxic and hypoxic conditions. Total RNA was extracted by using RNase Spin column (Qiagen, USA). VEGF expression was investigated by Northern blot analysis. Northern blot hybridization was performed using $^{32}$P-labeled VEGF cDNA probe and $^{32}$P-labeled EPO cDNA probe. The Northern blotting was performed by the conventional method well known to those in the art (Sambrook et al., Molecular cloning, 1989).

Figure 17:
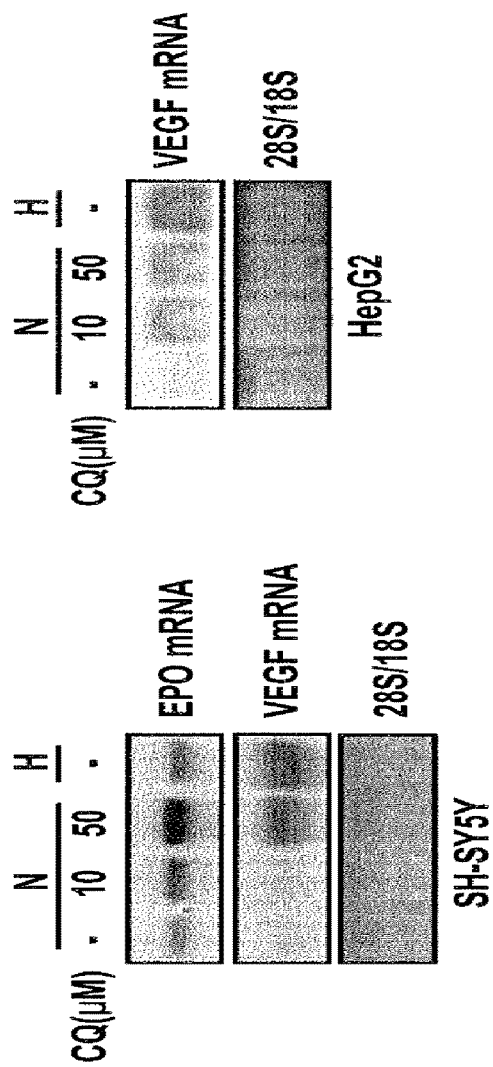
FIG. 17 is a diagram illustrating the expressions of VEGF and EPO by CQ and TPEN.

As a result, CQ increased expressions of VEGF and EPO in normoxic condition (FIG. 17).

EXAMPLE 7

Effects of CQ and its Derivatives on Angiogenesis

The present inventors performed CAM (choriallantoic membrane) assay (Cho, H. et al., Oncol Rep. 11(1):191-195, 2004) to examine the effect of CQ and its derivatives on angiogenesis. Particularly, the fertilized egg was incubated in a 37° C. 55% humid incubator. 10 days later, the egg albumin was removed by using a 2 ml hypodermic syringe in order to separate CAM and yolk sac from the shell membrane. On 10.5$^{th}$ day, the egg shell was removed (1 cm$^2$). To investigate angiogenic capacity of CQ and its derivatives, the sterilized circulation filter paper (0.5 cm, diameter, Whatmann, UK) containing VEGF (10 ng), CQ (10, 50 μM solution 10 μl: 30.6 ng, 152.8 ng), 5,7-diiodo-8-hydroxyquinoline (10, 50 μM solution 10 μl: 39.7 ng, 198.5 ng) and 5,7-dibromo-8-hydroxyquinoline (10, 50 μM solution 10 μl: 30.3 ng, 151.5 ng) was dried at room temperature and then applied to CAM (choriallantoic membrane) at Y-point of blood vessels. Three days later, 1-2 ml of 10% fat emulsion was injected into chorioallantoic membrane, followed by observation under a microscope.

Figure 18:
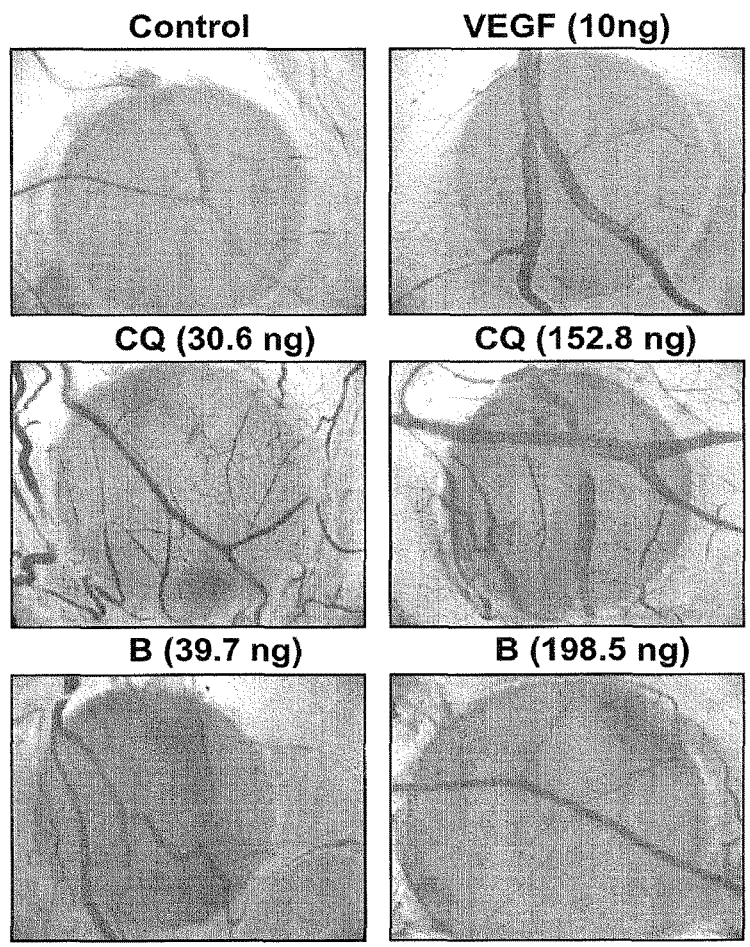
FIG. 18 is a diagram illustrating the angiogenesis induced by CQ and its derivatives.

As a result, CQ and its derivatives (5,7-diiodo-8-hydroxyquinoline and 5,7-dibromo-8-hydroxyquinoline) were confirmed to promote angiogenesis (Table 1 and FIG. 18).

TABLE 1

|   |   | Amount (ng) | Angiogenesis/total (No.) | Angiogenic ratio (%) |
|---|---|---|---|---|
| CQ | 5-chloro-7-iodo-8-quinolinol (Clioquinol): mw 305.50 | 30.6 152.8 | 8/12 8/12 | 67 67 |
| B | 5,7-diiodo-8-hydroxyquinoline (Indoquinol): mw 396.96 | 39.7 198.5 | 5/7 4/6 | 70 67 |
| C | 5,7-dibromo-8-hydroxyquinoline (Broxyquinoline): mw 302.96 | 30.3 151.5 | 4/6 3/5 | 67 60 |

INDUSTRIAL APPLICABILITY

As explained hereinbefore, CQ and its derivatives of the present invention inhibits HIF-1α (hypoxia-inducible factor-1 alpha) ubiquitination in normoxic cells and thus accumulates HIF-1α. In addition, CQ and its derivatives inhibit FIH-1 activity and thereby increase transactivation activity of HIF-1α and resultantly increase expressions of HIF-1α target genes VEGF (vascular endothelia growth factor) and EPO (erythropoietin). Therefore, CQ and its derivatives of the invention can be effectively used as a therapeutic agent for ischemic diseases.

SEQUENCE LIST TEXT

SEQ. ID. NO: 1 is a sequence of VEGF forward primer.
SEQ. ID. NO: 2 is a sequence of VEGF reverse primer,
SEQ. ID. NO: 3 is a sequence of 18S forward primer,
SEQ. ID. NO: 4 is a sequence of 18S reverse primer, Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method of treating ischemic disease by inducing angiogenesis in a subject, comprising:
    administering an effective amount of clioquinol or a derivative of clioquinol selected from the group consisting of 5-chloroquinolin-8-yl acetate, 5,7-diiodo-8-hydroxyquinoline, 5,7-dibromo-8-hydroxyquinoline and 8-hydroxyquinoline as an active ingredient to the subject;
    and detecting increased angiogenesis in the subject, thereby treating ischemic disease by inducing angiogenesis in the subject.

2. The method of claim 1, wherein the ischemic disease is selected from a group consisting of ischemic heart disease, ischemic brain disease and ischemic limb injury.

3. A method of inducing angiogenesis in a subject in need thereof, comprising administering an effective amount of clioquinol or a derivative of clioquinol selected from the group consisting of 5-chloroquinolin-8-yl acetate, 5,7-diiodo-8-hydroxyquinoline, 5,7-dibromo-8-hydroxyquinoline and 8-hydroxyquinoline to the subject.

4. The method of claim 3, wherein the clioquinol or the derivative of clioquinol activates hypoxia inducible factor-1α (HIF-1α).

5. The method of claim 3, wherein the clioquinol or the derivative of clioquinol inhibits factor inhibiting hypoxia-inducible factor-1α(FIH-1).

6. The method of claim 3, wherein the clioquinol or the derivative of clioquinol induces expression of vascular endothelial growth factor (VEGF) or erythropoietin (EPO).

7. A method of treating ischemic disease by inducing angiogenesis in a subject comprising administering an effective amount of a derivative of clioquinol selected from the group consisting of 5-chloroquinolin-8-yl acetate, 5,7-diiodo-8-hydroxyquinoline, 5,7-dibromo-8-hydroxyquinoline, and 8-hydroxyquinoline as an active ingredient to the subject.

8. The method of claim 7, wherein the ischemic disease is selected from the group consisting of ischemic heart disease, ischemic brain disease and ischemic limb injury.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: VEGF sense primer

```
<400> SEQUENCE: 1
ccatgaactt tctgctgtct t                                              21

<210> SEQ ID NO 2
<211> LENGTH: 20
<212> TYPE: DNA
<213> ORGANISM: Artificial Sequence
<220> FEATURE:
<223> OTHER INFORMATION: VEGF antisense primer

<400> SEQUENCE: 2
atcgcatcag gggcacacag                                                20

<210> SEQ ID NO 3
<211> LENGTH: 24
<212> TYPE: DNA
<213> ORGANISM: Artificial Sequence
<220> FEATURE:
<223> OTHER INFORMATION: 18S primer

<400> SEQUENCE: 3
accgcagcta ggaataatgg aata                                           24

<210> SEQ ID NO 4
<211> LENGTH: 20
<212> TYPE: DNA
<213> ORGANISM: Artificial Sequence
<220> FEATURE:
<223> OTHER INFORMATION: 18S antisense primer

<400> SEQUENCE: 4
ctttcgctct ggtccgtctt                                                20
```